United States Patent
Terashima et al.

(10) Patent No.: US 9,816,955 B2
(45) Date of Patent: Nov. 14, 2017

(54) LIQUID SAMPLE MEASURING SYSTEM AND MEASURING DEVICE

(71) Applicant: PANASONIC HEALTHCARE HOLDINGS CO., LTD., Minato-Ku, Tokyo (JP)

(72) Inventors: Noriyoshi Terashima, Kanagawa (JP); Teppei Shinno, Ehime (JP); Masataka Nadaoka, Ehime (JP); Yoshimasa Oda, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

(21) Appl. No.: 14/367,938

(22) PCT Filed: Dec. 26, 2012

(86) PCT No.: PCT/JP2012/008310
§ 371 (c)(1),
(2) Date: Jun. 23, 2014

(87) PCT Pub. No.: WO2013/099238
PCT Pub. Date: Jul. 4, 2013

(65) Prior Publication Data
US 2015/0125938 A1    May 7, 2015

(30) Foreign Application Priority Data
Dec. 26, 2011   (JP) ................. 2011-283197

(51) Int. Cl.
*G01N 27/327* (2006.01)
*G01N 33/487* (2006.01)

(52) U.S. Cl.
CPC ..... *G01N 27/3273* (2013.01); *G01N 27/3272* (2013.01); *G01N 27/3274* (2013.01); *G01N 33/48792* (2013.01)

(58) Field of Classification Search
CPC ......... G01N 27/3273; G01N 33/48792; G01N 27/3274; G01N 27/273272
See application file for complete search history.

(56) References Cited

U.S. PATENT DOCUMENTS 7,738,934 B2   6/2010 Takase et al.
8,239,582 B2   8/2012 Elder
(Continued)

FOREIGN PATENT DOCUMENTS

CN   101036575 A   9/2007
CN   102197304 A   9/2011
(Continued)

OTHER PUBLICATIONS

Office Action from the corresponding Chinese Patent Application No. 201280064313.2 dated Apr. 1, 2015.
(Continued)

*Primary Examiner* — Sam P Siefke
(74) *Attorney, Agent, or Firm* — Shinjyu Global IP

(57) ABSTRACT

An liquid sample measuring system includes a measuring device including a measuring section which measures biological information from liquid sample of a living subject within a housing in which a biosensor, on which the liquid sample of the biological body is deposited, is detachably mounted and a movement measuring section which measures movement information of the housing within the housing, and an administrating device including a movement determining section which determines whether or not a degree of the movement of the housing is within an allowable range by analyzing the movement information received from the measuring device.

17 Claims, 12 Drawing Sheets

(56) References Cited

U.S. PATENT DOCUMENTS

| | | |
|---|---|---|
| 8,372,351 B2 | 2/2013 | Ow-Wing |
| 8,450,078 B2 | 5/2013 | Dennis et al. |
| 8,597,570 B2 | 12/2013 | Terashima et al. |
| 2007/0219436 A1 | 9/2007 | Takase et al. |
| 2010/0305421 A1 | 12/2010 | Ow-Wing |
| 2011/0151491 A1 | 6/2011 | Dennis et al. |
| 2011/0196218 A1 | 8/2011 | Nomura et al. |
| 2011/0257496 A1 | 10/2011 | Terashima et al. |
| 2011/0296158 A1 | 12/2011 | Elder |
| 2012/0179017 A1 | 7/2012 | Satou et al. |
| 2013/0216434 A1 | 8/2013 | Ow-Wing |
| 2013/0267017 A1 | 10/2013 | Dennis et al. |
| 2014/0046160 A1 | 2/2014 | Terashima et al. |
| 2015/0125938 A1 | 5/2015 | Terashima et al. |

FOREIGN PATENT DOCUMENTS

| | | |
|---|---|---|
| JP | 2005-267135 A | 9/2005 |
| JP | 2007-244736 A | 9/2007 |
| JP | 2007-323373 A | 12/2007 |
| JP | 2008-011865 A | 1/2008 |
| JP | 2010-085258 A | 4/2010 |
| JP | 2010-201006 A | 9/2010 |
| JP | 2010-236933 A | 10/2010 |
| JP | 2010-266217 A | 11/2010 |
| JP | 2011-501681 A | 1/2011 |
| JP | 2011-134106 A | 7/2011 |
| JP | 2011-209246 A | 10/2011 |
| JP | 2011-252851 A | 12/2011 |
| JP | 2015-163904 A | 9/2015 |
| WO | 2009/049252 A1 | 4/2009 |
| WO | 2010/052849 A1 | 5/2010 |
| WO | 2011/033876 A1 | 3/2011 |

OTHER PUBLICATIONS

Office Action from the corresponding European Patent Application No. 12861365.0 dated Apr. 2, 2015.
International Search Report of Int'l Appln. No. PCT/JP2012/008310 dated Feb. 12, 2013.
Office Action from the corresponding Japanese Patent Application No. 2013-551246 dated Mar. 10, 2015.

LIQUID SAMPLE MEASURING SYSTEM AND MEASURING DEVICE

PRIORITY

This application claims priority to International Application International Application PCT/JP2012/008310, with an international filing date of Dec. 26, 2012 which claims priority to Japanese Patent Application No. JP2011-283197 filed on Dec. 26, 2011. The entire disclosures of International Application PCT/JP2012/008310 and Japanese Patent Application No. JP2011-283197 are hereby incorporated herein by reference.

TECHNICAL FIELD

The present invention relates to a measuring device and a liquid sample measuring system including the measuring device which measures biological information from a liquid sample of living subject.

BACKGROUND

There has been a hand-held type of a measuring device of measuring liquid sample of a living subject. The measuring device can easily perform measuring the liquid sample, which was conventionally performed by a large clinical measuring device. For example, a user can measure his/her liquid sample daily at home by the measuring device. Also, a nurse can measure the liquid sample of a patient by using the measuring device on the bedside of a room or an examination room of a medical institution.

Because of introduction of various measuring technologies, the hand-held type measuring device has provided lessening amount of a sample which is needed for measuring and shortening time for measuring, and thus is shaped to enhance convenience.

However, accuracy of the result of measuring with the existing measuring device fluctuates due to various factors.

For example, in a case in which the measuring device is a blood glucose measuring device which measures glucose concentration in blood, there are factors for the fluctuation in the result of measuring, as follows.

First, an interfering substance in the blood and a state of the blood influence the result of measuring. For a blood glucose monitor which is for measuring whole blood, a fact that a ratio of blood cell in the blood which changes on the basis of a condition of a subject person or a disease state influences the result of measuring the glucose concentration is well known. Also, it is known that there is a reagent among reagents used for measuring the blood glucose which reacts with the maltose in the blood and shows higher concentration than concentration of glucose as principally a measuring object in a case in which the maltose is provided to the blood by dialysis or infusion from dialysis fluid.

There are countermeasures in which a measuring method with correcting by hematocrit value as a blood cell ratio in the blood and a reagent which is less influenced by the maltose are employed, in order to decrease the fluctuation in the result of measuring due to the factors like this.

Second, fluctuation in a manufacturing process of the biosensor influences the result of measurement. The biosensor (blood glucose sensor) is used as being completely disposable for measuring the blood glucose. Manufacturers manufacture blood glucose sensors a lot every day in response to demands of measuring the blood glucose being performed multiple times a day. For this reason, the fluctuation in quality of the biosensor (blood glucose sensor) happens due to changes in environment and materials in the manufacturing process of the biosensor.

There are countermeasures in which materials or a process of manufacturing to minimize the fluctuation in manufacturing the biosensor, and switching measuring parameters by considering the fluctuation are employed, in order to decrease the fluctuation in the result of measuring due to the factors.

Third, a state of using a measuring device main body influences the result of measuring. The hand-held type of the measuring device is easily brought between user's home, outside, and each room of a hospital. For this reason, constituent elements such as electric parts and mechanical parts in the measuring device main body are damaged due to physical impact from outside such as dropping. Then, it is possible that the measuring device cannot measure in a normal way.

There are countermeasures in which notifying, if necessary, is employed by measuring a degree of the impact and determining whether or not the degree of the impact is large enough to influence accuracy of measuring the blood glucose (for example, see Patent Literature 1: Japanese Patent Application Publication No. 2011-209246).

As mentioned above, effort has been made in suppressing the fluctuation in the result of measuring by finding causes of the fluctuation in the result of measuring due to the various factors.

However, in the above mentioned effort or the like, the countermeasure has not been made to reveal the influence to decreasing the accuracy in measuring due to user's movement (handling), when measuring the liquid sample is actually performed.

In other words, there is a problem in the handling when the user measures the liquid sample, and that causes the fluctuation in the result of measuring. In this case, the measuring device shows a wrong value as the result of measuring, or has an error for movement of measuring. However, the above mentioned measuring device has problems in not performing an appropriate countermeasure by specifying problems of the handling.

Then, the description below has an objective in providing a liquid sample measuring system and a measuring device for performing the appropriate countermeasure by specifying the problem of use's handling.

SUMMARY

A liquid sample measuring system which is described hereinafter includes a measuring device including a measuring section which measures biological information from liquid sample of a living subject within a housing in which a biosensor, on which the liquid sample of the biological body is deposited, is detachably mounted and a movement measuring section which measures movement information of the housing within the housing, and an administrating device including a movement determining section which determines whether or not a level of the movement of the housing is within an allowable range by analyzing the movement information received from the measuring device.

DETAILED DESCRIPTION

A liquid sample measuring system as embodiments of the present invention is described in detail hereinafter with reference to the figures.

First Embodiment

Figure 1:
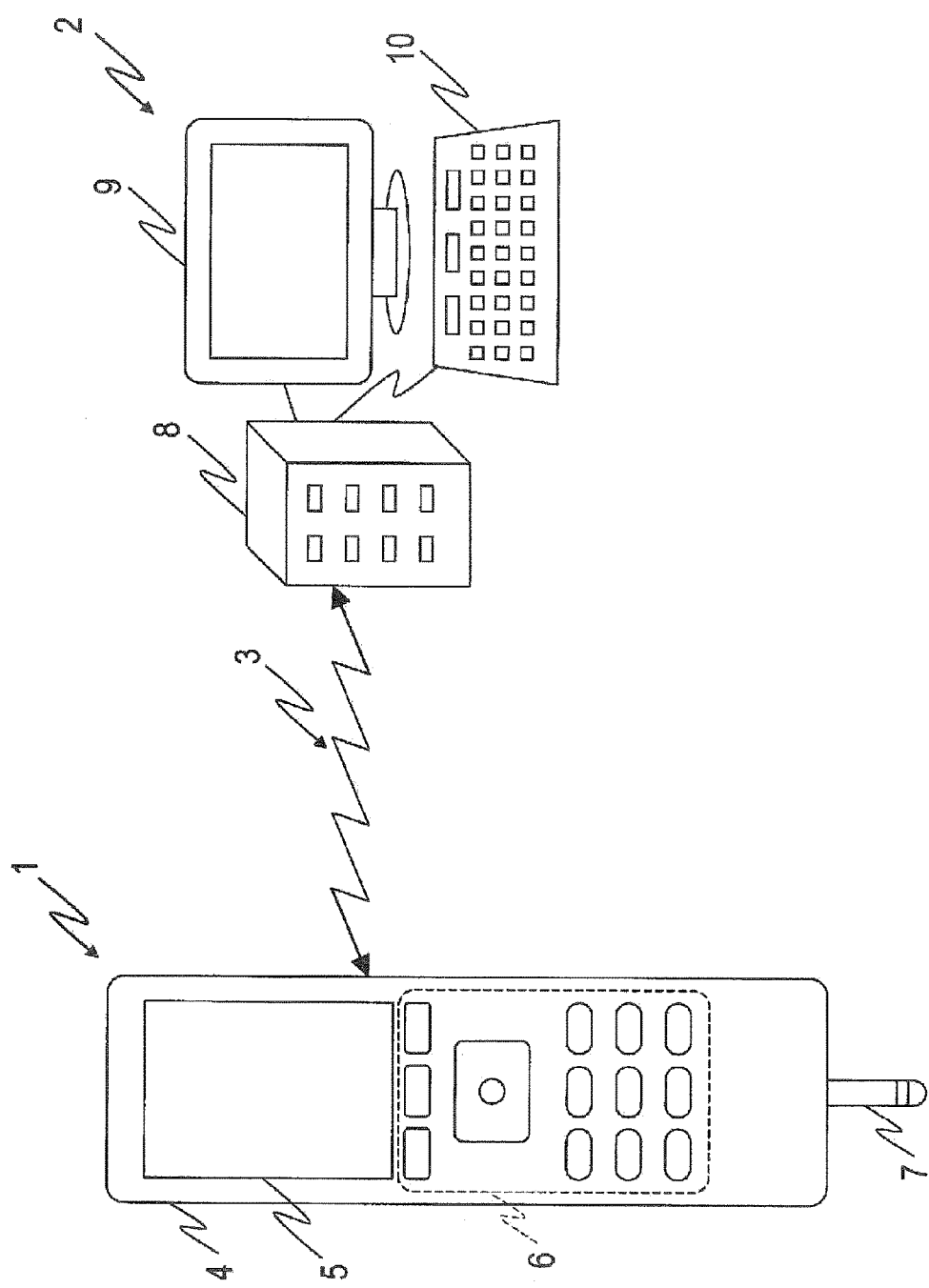
FIG. 1 is a view showing an arrangement of a liquid sample measuring system of a first embodiment.

FIG. 1 is a view showing an entire arrangement of the liquid sample measuring system of a first embodiment. As shown in FIG. 1, the liquid sample measuring system includes a measuring device 1 and an administrating device 2. The measuring device 1 and the administrating device 2 communicate by being connected each other with a wired connection by a cable, or connected wirelessly by radio wave or infrared ray. Alternatively, it is fine that there is Internet or a network of an intranet between the measuring device 1 and the administrating device 2, and that measuring device 1 and a network access point, and an administrating device 2 and the network access point are connected with a wired or wireless connection. Hereinafter, a communication line 3 is a collective term for the wired and wireless connections, and connections via networks.

The measuring device 1 is a hand-held type measuring device. The measuring device 1 includes a device main body (housing) 4, a display section 5, and an input section 6. On the device main body 4 of the measuring device 1, a biosensor 7 which is disposable is mounted or dismounted.

The device main body 4 is formed in a compact shape which a nurse or a patient as a user can hold with one hand.

The administrating device 2 includes a device main body 8, a display section 9, and an input section 10. It is fine that all, or any combination of, the device main body 8, the display section 9, and the input section 10, are entirely unitarily formed. Also, it is fine that the device main body 8, the display section 9, and the input section 10 are disposed in a place in a state in which entirely connected by a cable, or disposed remotely in a state via a network.

For example, the administrating device 2 being an ordinary personal computer is one example of the former. Also, an arrangement in which the device main body 8 is a server device disposed in a server room, the display section 9 is a monitor disposed on a wall of a nurse station of a hospital, and the input section 10 is a touch panel which enables inputting by touching on the monitor in one example of the latter.

When the liquid sample measuring system is used, for example, in a hospital, the measuring device 1 is carried by a nurse to go around medical wards, and the administrating device 2 is disposed at a nurse station for use.

Figure 2:
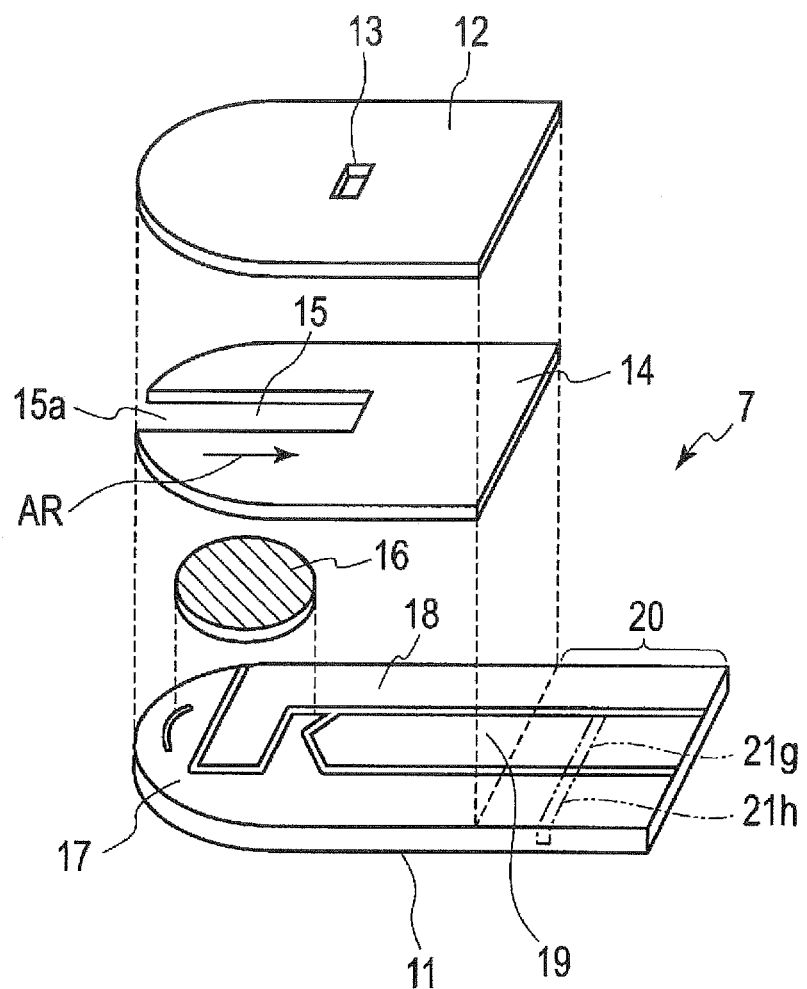
FIG. 2 is a exploded diagrammatic view of a biosensor.

Next, the biosensor 7 which is disposable and is mounted to the measuring device 1 is described with reference to FIG. 2. FIG. 2 is an exploded diagrammatic view of the biosensor 7 mounted to the measuring device 1.

The biosensor 7 include an insulated substrate 11 made of polyethylene terephthalate or the like (hereinafter simply substrate 11). On a surface of the substrate 11, a conductive layer is formed. The conductive layer is made of, for example, noble metal such as gold and palladium, or made of a conductive material such as carbon. The conductive layer is formed on the substrate 11 by a screen printing method or a sputtering vapor deposition method. The conductive layer can be formed entirely on the substrate 11 or at least partially on the substrate 11. Also, the biosensor 7 includes an insulated substrate 12 on an upper surface thereof. The substrate 12 includes an air opening 13 at a middle part thereof. Between the substrate 11 and the substrate 12, a spacer 14 including a notch part is sandwiched. The substrate 11, the spacer 14, and the substrate 12 unitarily constitute the biosensor 7.

On the substrate 11, a counter electrode 17, a measurement electrode 18, and a detection electrode 19 are formed by slits dividing the conductive layer. Each of the electrodes 17, 18, 19 is formed at least on a part of the substrate 11. Also, it is fine that each of the electrodes 17, 18, 19 is connected to the measuring device 1 through lead wires in a state in which the biosensor 7 is mounted to the device main body 4 of the measuring device 1.

The spacer 14 is disposed so as to cover the counter electrode 17, measurement electrode 18, and detection electrode 19 on the substrate 11. A sample supply route 15 is formed by a notch part being rectangular and configured on a front edge and a center of the spacer 14. Also, the liquid sample is deposited at a sample spotting part 15a which is a tip the sample supply route 15. When the liquid sample is deposited on the sample spotting part 15a, the liquid sample is suctioned towards an air opening 13 of the substrate 12 (in a direction of an arrow AR in FIG. 2) by capillary action.

The reagent layer 16 has a size and a shape to cover the counter electrode 17, measurement electrode 18, and the detection electrode 19 which are exposed from the notch part of the spacer 14.

The reagent layer 16 includes an oxidation reduction enzyme and an electron acceptor. The oxidation reduction enzyme and the lector acceptor are dissolved and react with the liquid sample (in the present embodiment, blood from a human body) which is suctioned by the sample supply route 15. After the reaction, the measurement device 1 electrochemically oxidizes the electron acceptor, which has been reduced. The measuring device 1 measures the biological information (in the present embodiment, the blood glucose concentration in the blood) in the liquid sample on the basis of the electric current obtained by the oxidation. This chain of the reaction is read by electric current with the electrochemical changes by the counter electrode 17, the measurement electrode 18, and the detection electrode 19.

Also, an identifying part 20 is a member which identifies differences in output characteristic depending on kinds and production lot of the biosensor 7 by the device main body 4. A combination of slit 21g and a slit 21h are configured at a part corresponding to the identifying part 20 of the counter electrode 17 and the detection electrode 19. By this, the device main body 4 can identify the difference of the electrical output characteristic of each biosensor 7.

The counter electrode 17, the measurement electrode 18, the counter electrode 17, and detection electrode 19 are arranged in the order from the sample spotting part 15a in the flow direction of the liquid sample (arrow AR) on the substrate 11 of the biosensor 7. The configuration of the counter electrode 17 and the measurement electrode 18 can be switched Also, there is a prescribed distance between the measurement electrode 18 and the detection electrode 19 in the direction of the liquid sample flowing. By this, the detection electrode 19 can identify whether or not the liquid sample is surely and adequately suctioned.

Figure 3:
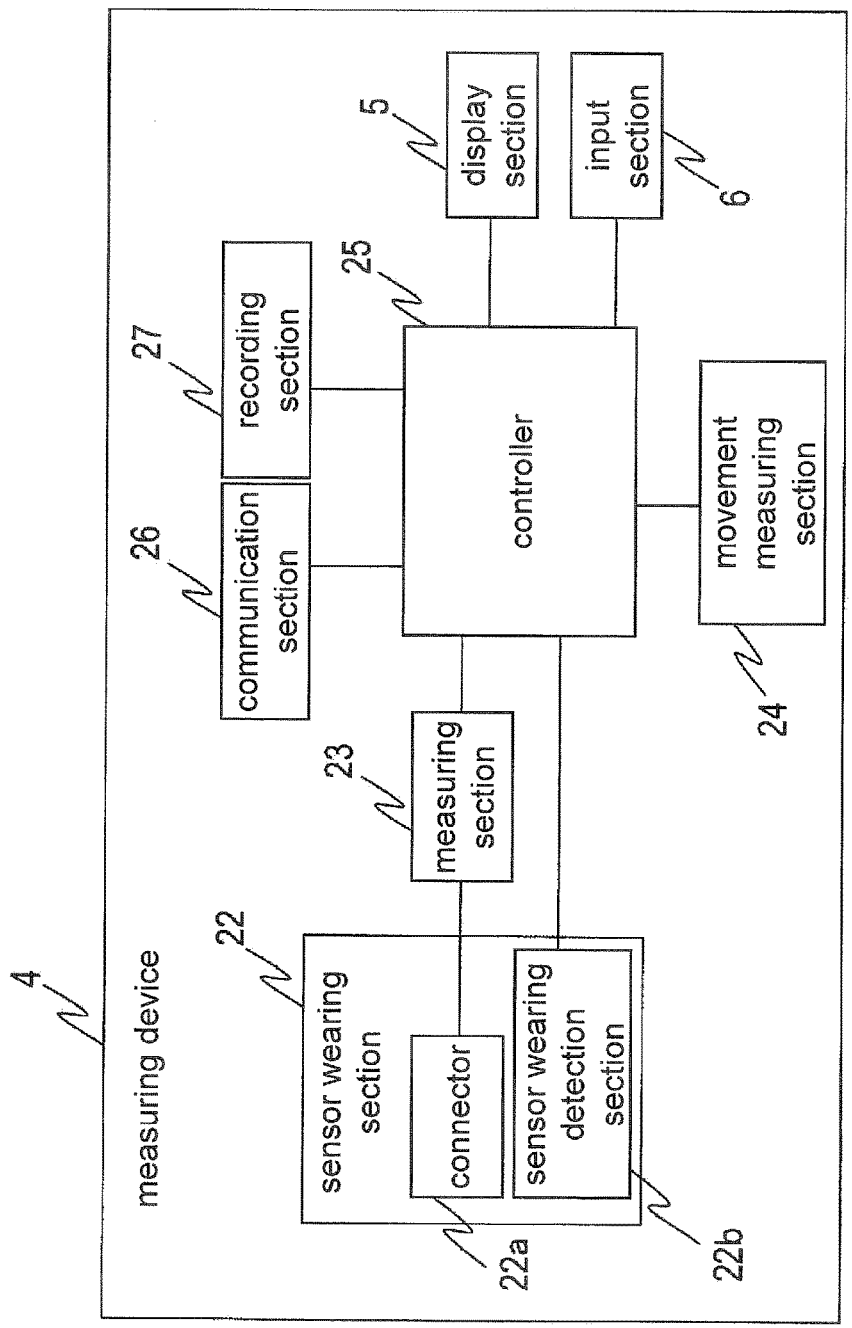
FIG. 3 is a block diagram of the measuring device of the first embodiment.

Next, constituent elements of the measuring device 1 are described with reference to FIG. 3. FIG. 3 is a block diagram showing the measuring device 1. As shown in FIG. 3, the measuring device 1 includes a sensor wearing part 22, a measuring section 23, a movement measuring section 24, a controller 25, a display section 5, an input section 6, a communication section 26, and a recording section 27 in the device main body 4.

Further, in the sensor wearing part 22, a connector 22a and a sensor wearing detection section 22b are disposed. The connector 22a is capable to connect electrically the counter electrode 17, the measurement electrode 18, and the detection electrode 19 of the biosensor 7, when the biosensor 7 is mounted. The sensor wearing detection section 22b is to detect that the biosensor 7 is mounted to the sensor wearing part 22.

The sensor wearing detection section 22b detects that the biosensor 7 is equipped and transmits to the controller 25. The means by the sensor wearing detection section 22b is, for example, a mechanical electrical switch which is capable of detecting that the biosensor 7 is equipped by the electrical switch being pushed to conduct electrically while the object (biosensor 7) is equipped. Other than that, the sensor wearing detection section 22b can be any means, such as an optical sensor, as long as the existence of the object at the sensor wearing part 22 can be detected.

Alternatively, the sensor wearing detection section 22b can be an additional electrical circuit which is connected to the connector 22a. In this case, when electrical conduction is detected between the connector 22a and at least one of the counter electrode 17, the measurement electrode 18, and the detection electrode 19 at the biosensor 7, the sensor wearing detection section 22b determined that the biosensor 7 is mounted to the device main body 4.

The measuring section 23 receives an instruction from the controller 25 and measures the biological information from the liquid sample of the living subject which is deposited on the biosensor 7. For example, when the blood is deposited on the biosensor 7, electric voltage or current is applied to each of the electrodes of the biosensor 7 via the connector 22a. The measuring section 23 measures the glucose concentration in the blood from value of the electric voltage or the current obtained in corresponding to the application of the electric voltage.

The movement measuring section 24 receives an instruction from the controller 25 and measures amount of movement of the device main body 4. The movement measuring section 24 transmit movement information as the amount of the movement to the controller 25.

The controller 25 controls the measuring device 1 entirely. Information is input from the sensor wearing detection section 22b, the measuring section 23, the movement measuring section 24, and the input section 6 to the controller 25. The controller 25 instructs the measuring section 23, the display section 5, the communication section 26, and the recording section 27 on the basis of the input information.

The display section 5 functions on the basis of an instruction from the controller 25. The display section 5 displays the glucose concentration as the biological information measured by the measuring section 23. Also, the display section 5 displays various information to the user.

The input section 6 is a device in which the movement instruction or identification number is input from the user. Input section 6 is, for example, a button disposed on the device main body 4. Alternatively, the input section 6 may be an optical reading device such as a barcode reader. Alternatively, the input section 6 is an input by a wireless communication such as RF-ID, or a voice recognition. The input section 6 in the present embodiment is configured as a combination of these input devices. Also, the information being input to the input section 6 is transmitted to the controller 25.

The communication section 26 receives an instruction from the controller 25 and receives from and transmits to other devices such as a server or a personal computer via the communication line 3. For example, the communication section 26 transmits the identification number which has been input to the input section 6 and the glucose concentration which has been measured by the measuring section 23 to other devices. Also, the communication section 26 receives a list of the identification number from other devices.

The recording section 27 records, by receiving via the controller 25, the result of measuring transmitted by the measuring section 23, the movement information transmitted by the movement measuring section 24, the information input by the input section 6, and the information received by the communication section 26. The recording and playing the data to the recording section 27 is controlled by the controller 25.

When the user starts measuring the liquid sample by using the aforementioned measuring device 1 and the biosensor 7, inputting identification of the user (nurse) as a measurer, identification of the patient as the subject person, and identification of the biosensor 7 is performed by the input section 6. The input of the identifications may be performed by the user pushing the button of the input section 6. Also, in a case where the barcode reader is configured on the input section 6, it is fine that inputting each of the identifications is input by reading the barcode configured on each. Also, it if fine that each of the identifications is obtained by a close distance wireless communication from RF-ID tags configured on each. When inputting the identifications is complete, preparation for measuring is complete.

When the preparation for measuring is complete, the user mounts the biosensor 7 next. The biosensor 7 is mounted to the sensor wearing part 22, and the completion of equipping is detected by the sensor wearing detection section 22b and transmitted to the controller 25. The controller 25 keeps time at which when the completion of mounting by the sensor wearing detection section 22 is detected is transmitted as time of mounting the sensor. Then, the controller 25 instructs starting measuring the liquid sample to the measuring section 23 of the controller 25.

The measuring section 23 to which the controller 25 has instructed starting measuring starts applying electric voltage to the counter electrode 17, the measurement electrode 18, and the detection electrode 19 of the biosensor 7 via the connector 22a. At this time, the blood has not been deposited on the sample spotting part 15a of the biosensor 7.

When the blood is deposited on the sample spotting part 15a by the user, the blood is suctioned towards the inside of the sample supply route 15 by capillary action, and expands in a direction towards the air opening 13. After that, the blood after expanding reaches one, which is configured closest to the sample spotting part 15a, of the counter electrode 17, the measurement electrode 18, and the detection electrode 19. Responding to this, the measuring section 23 detects the deposition of the blood by changes in a response characteristic of the electric voltage obtained via the connector 22a. The measuring section 23 transmits the deposition of the blood to the controller 25. By this, the controller 25 keeps the time at which when the blood is deposited is detected as time of sample deposition.

The measuring section 23 starts measuring the glucose concentration in the blood, when a set time from the time of the sample deposition elapses, or when further changed occur in the response characteristic of the electric voltage in the counter electrode 17, the measurement electrode 18, and the detection electrode 19. Then, the measuring section 23 transmits starting measuring to the controller 25. Responding to this, the controller 25 keeps the time as time of starting measuring.

The time between the time of the sample deposition and the time of starting measuring is needed for the blood, which is deposited by the user, to expand adequately in the sample supply route 15, to melt the reagent layer 16, and to react.

The measuring section 23 applies the electric voltage at least one time between a plurality of the electrodes 17, 18 after starting measuring. The measuring section 23 obtains response value, at least one time, of the electric current accompanying electrochemical changes during the application of the electric voltage, and keeps as a current profile. Then, the measuring section 23 specifies the glucose concentration by using the current profile with Cottrell equation or other algorithm, and transmit the glucose concentration to controller 25 as the result of measuring. The controller 25 keeps time at which the glucose concentration which has been measured by the measuring section 23 is transmitted as time of ending measuring.

The controller 25 instructs the display section 5 to display the glucose concentration which has been measured. At the same time, the controller 25 displays candidates of information to be associated with the glucose concentration, and enables the user to select by using the input section 6. Here, the candidate of the information is for seeing the situation of measuring when confirming the result of measuring the glucose concentration, such as information regarding meal including before meal or after meal. The user can separately set what kinds of information are selectable. Also, not only is the candidate of the information selected, but it is also fine that the user can input a line of texts by using the input section 6.

The controller 25 records in the recording section 27 the information regarding measuring as a batch of measuring administration data, after the user completes inputting. In the measuring administration data include the identification of the measurer, the identification of the subject person, and the identification of the biosensor 7. Also, the measuring administration data includes time of mounting the sensor, the time of the sample deposition, time of starting measuring, and time of ending measuring. Further, the measuring administration data includes the glucose concentration, regarding information which the user selects, and the information of the movement output by the movement measuring section 24.

Also, the controller 25 monitors the glucose concentration which is measured. The controller 25 adds an abnormal value flag showing that matter to the measuring administration data, when the glucose concentration being measured is an abnormal value which cannot be normal obtained, or when the glucose concentration is a value outside a range that the user sets. The controller 25 notifies the user by displaying the detection of the abnormal value by the display section 5, when the abnormal value flag is added.

Next, the movement measuring section 24 is described. The movement measuring section 24 is realized by, for example, a three-dimensional acceleration sensor disposed in the device main body 4. The number of the acceleration sensor can be one or plural. Also, a gyro sensor can be used instead of the acceleration sensor, or any sensor, as long as changes in posture and moving distance (amount of moving) of the device main body 4 in the direction of the gravity are detected.

Figure 4:
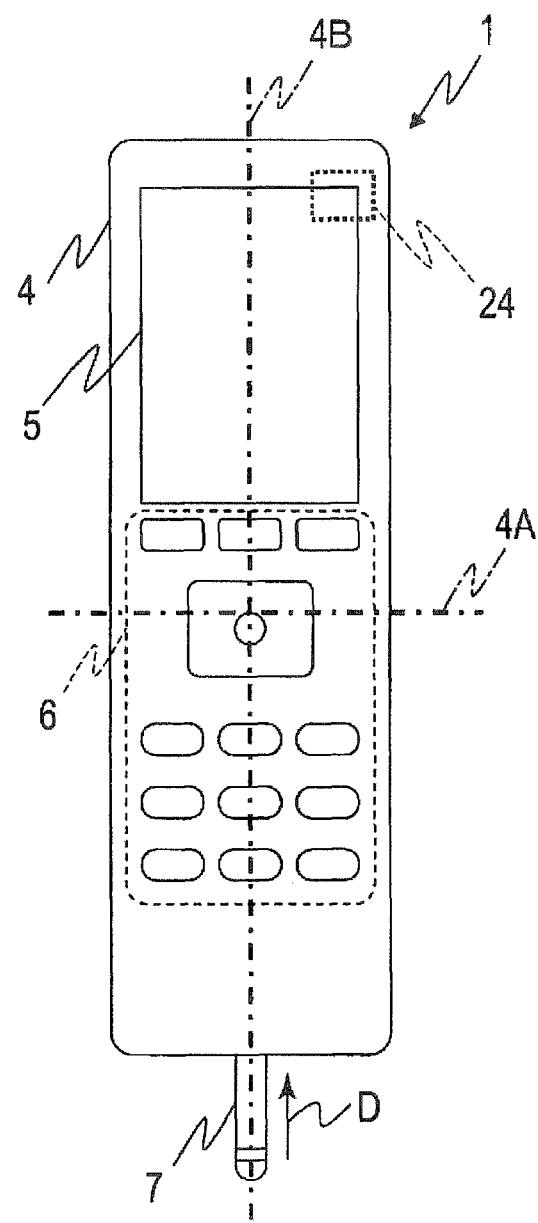
FIG. 4 is a front view showing an example of the measuring device including a movement measuring section.

FIG. 4 shows an example in which an acceleration sensor is disposed as the movement measuring section 24 in the device main body 4. The acceleration sensor is disposed at an end opposite to an end in a longitudinal direction to which the biosensor 7 is mounted. Also, the acceleration sensor is disposed at a place off from a width-direction center line 4A and a longitudinal-direction center line 4B of the device main body 4. Here, the longitudinal direction of the device main body 4 is a direction D in which the biosensor 7 is mounted to the device main body 4. Also, the place at which the acceleration sensor is disposed is off from a barycenter of weight of the device main body 4.

The posture and the movement of the biosensor 7 are detected accurately by the disposition of the acceleration sensor. Because the sample which is deposited on the biosensor 7 is liquid, a position and a direction of expanding of the liquid change due to the posture and the movement of the biosensor 7. There are cases where the direction and the position of expanding affect the result of measuring the glucose concentration. Because of this, the acceleration sensor is disposed at the place being effectual to monitor the position and the direction of expanding of the liquid, namely the place being off from the width-direction center line 4A and the longitudinal-direction center line 4B of the device main body 4.

Figure 5:
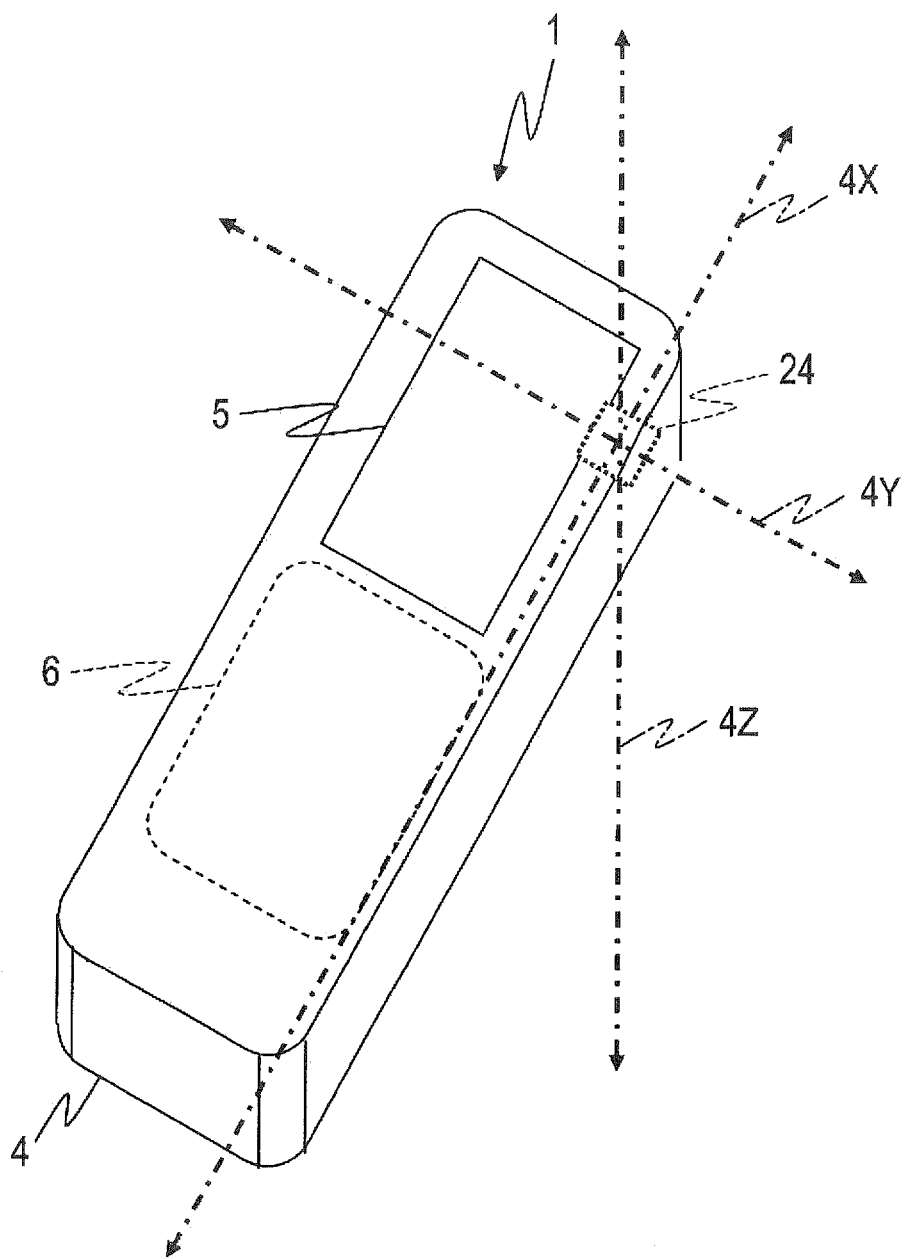
FIG. 5 is a diagonal perspective view showing an example of the measuring device including the movement measuring section.

FIG. 5 shows a three dimensional axes being overlapped on a pattern view of the measuring device 1. Against the device main body 4, a longitudinal direction is X axis 4X, a short direction is Y axis 4Y, and a height direction is Z axis 4Z. An ordinary sensor which detects a degree of changes in the movement (amount of moving) per unit time for each of the three dimensional axes is used for the acceleration sensor configured as the movement measuring section 24.

It is fine as long as the movement measuring section 24 can detects the degree of the changes in the movement (amount of moving) per unit time for each of the three dimensional axes. Also, kinds of sensor are not limited to the acceleration sensor.

The movement measuring section 24 transmits to the controller 25 the degree of the changes in the movement (amount of moving) per unit time detected for each of the three dimensional axes as movement information while controller 25 instructs. Numerical expression of the degree of the changes in the movement can be absolute number or relative value. Also, it is fine as long as the movement information includes necessary and sufficient information to replicate the movement of the device main body 4 on the basis of the movement information. Also, an interval for transmitting the movement information, namely a sampling interval, is chosen to be an appropriate interval in order to also replicate the movement of the device main body 4.

As a typical example, the controller 25 instructs to the movement measuring section 24 that from the time of mounting sensor to the time of ending measuring, the movement information is measured. The period of time is the most efficient in analyzing the movement of the measuring device 1 due to user's handling by synchronizing the movement in measuring the glucose concentration. However, in a case where amount a memory as the recording section 27 is adequate, or in a case where the amount of the moving is transmitted real time to devices outside via the communication line 3, it is fine to instruct measuring the movement information other than in the period of time. By that, additional effect in which a way of using the measuring device 1 by analyzing user's handling other than the movement in measuring the glucose concentration is obtained can be attained. By this, the influence to the result of measuring, indirectly by the handling, in the period other than the period between the time of mounting the sensor and the time of ending measuring is considered.

The controller 25 instructs the communication section 26 to transmit the measuring administration data recorded in the recording section 27 to the administrating device 2 via the communication line 3 in a prescribed timing. The prescribed timing includes a case in which the user instructs to do and a case in which the controller 25 spontaneously does. In the case in which the user instructs transmitting the measuring administration data by the input section 6, when the communication section 26 establishes the communication with the administrating device 2 via the communication line 3, the communication section 26 immediately transmits the measuring administration data. When the communication section 26 does not establish the communication with the administrating device 2, the controller 25 instructs the communication section 26 to establish the communication with the administrating device 2. The communication section 26 transmits the measuring administration data after the communication is established. Alternatively, it is fine that the controller 25 plans proceeding in the controller 25 to transmit the measuring administration data when the communication section 26 establishes the communication with the administrating device 2 next time.

When the user instructs transmitting the measuring administration data, it is preferable that the controller 25 can select one or plurality of when the user measure, who measures, and whom is measured by using the display section 5 and the input section 6.

When the controller 25 spontaneously transmits the measuring administration data, the communication section 26 performs the transmission operation in either timing described below. The user can prescribe which timing the communication section 26 performs the transmission operation. The timing can be:

1) when the controller 25 records the measuring administration data in the recording section 27 after the glucose concentration is measured;
2) when the communication section 26 establishes the communication with the administrating device 2 via the communication line 3;
3) when the measuring administration data is requested by the administrating device 2 to be transmitted;
4) when the batter disposed in the device main body 4 is being charged;
5) when the power source of the measuring device 1 is instructed to be off; and
6) the glucose concentration measured by the measuring section 23 is determined to be abnormal.

In a case where transmitting the measuring administration data is scheduled in the timing in which the communication between the measuring device 1 and administration device 2 is not established, the communication section 26 performs establishing the communication between the communication section 26 and the administrating device 2 each time.

Figure 6:
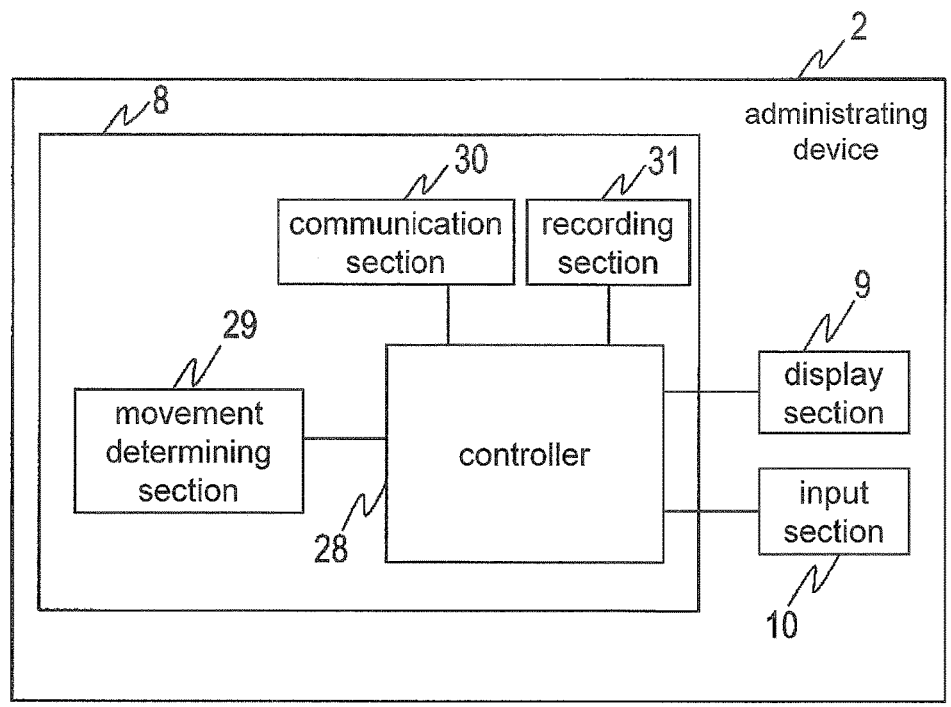
FIG. 6 is a block diagram showing an arrangement of an administrating device of the first embodiment.

Next, constituent elements of the administrating device 2 are described with reference to FIG. 6. FIG. 6 is a block diagram of the administrating device 2. As shown in FIG. 6, the administrating device 2 includes a device main body 8 including a controller 28, a movement determining section 29, a communication section 30, and a recording section 31, a display section 9, and an input section 10. The device main body 8 is realized by, for example, a personal computer or a server.

The controller 28 controls all the elements which constitutes the administrating device 2. The controller 28 can be realized by including an ordinary CPU, an operating system implemented there, a program, and the like.

The movement determining section 29 obtains the measuring administration data transmitted from the measuring device 1 by receiving the instruction form the controller 28. The movement determining section 29 analyzes and determines the movement information of the measuring device 1 by using the measuring administration data.

The communication section 30 performs the data transmission and reception with the administrating device 2, the measuring device 1 or the like via the communication line 3. The communication section 30 can be arranged to communication one-on-one with the measuring device 1 being particular, or to communicate one-to-many with a plurality of measuring devices 1.

The recording section 31 records various data and information. The recording section 31 is recordable of the measuring administration data transmitted from the measuring device 1. Also, the recording section 31 is recordable of patient information and nurse information input by the input section 10 or the like. Further, the recording section 31 is recordable of information presented to the user by the display section 9. The recording section 31 can be disposed in the device main body 8 as shown in the figure, but a large storage device which is externally connected can be used.

The display section 9 displays contents instructed by the controller 28. The display section 9 can be realized, for example, by a liquid crystal display.

The input section 10 is used by the user to input the instruction and the data to the controller 28. FIG. 1 shows a keyboard as an example, but not limited to this. The input section 10 can be realized by combining a pointing device such as a mouse and a reading device such as a barcode reader, an electric card reader, or a scanner.

The administrating device 2 performs various administration processes. The administrating device 2 administrates a plurality of the measuring devices 1. Also, the administrating device 2 administrates database of the measurer and the subject person. Also, the administrating device 2 administrates correction information of the biosensor 7. The administrating device 2 presents each administrating status to the user by using the display section 9.

The administrating device 2, for example, determines whether or not maintenance is necessary on the basis of a history of the use or a status of the use of the measuring device 1. By this, the administrating device 2 can present whether or not the maintenance is necessary to the user. The administrating device 2 can display a tendency in changes, in a chart, of the glucose concentration for each subject person by using a plurality of the results of measuring the glucose concentration. Further, the administrating device 2 calculates consumption of the disposable biosensor 7 which is consumable by extracting the identification of the biosensor 7 from the measuring administration data. By this, the administrating device 2 can present the inventory information of the biosensor 7, which the user can use, to the user by referring to the inventory information of the biosensor 7 with in a facility.

As one of various programs that the administrating device 2 implements, a handling analyzing program performing analyzing the handling of the user on the basis of the movement information of the measuring device 1 is included. The handling analyzing program is one of programs implemented by the controller 28. The administrating device 2 can use a processing device which performs dedicatedly the handling analyzing program. Because of this, a functional section which performs the handling analyzing program is shown as the movement determining section 29 in FIG. 6.

The controller 28 receives the measuring administration data which has received by the communication section 30 and which has been sent from the measuring device 1 by the communication section 30. The controller 28 records, as needed, the measuring administration data, which has been received by the communication section 30, in the recording section 31. At this time, the controller 28 records each of the measuring administration data in the recording section 31 by labeling in order for the measuring administration data to be extractable for each of the measurer identifications. By this, the controller 28 administrates the measuring administration data for each of the measurer.

The controller 28 instructs the movement determining section 29 to analyze the movement information, when instructed from the user via the input section 10, or spontaneously. When instructed by the user to analyze the movement information, the controller 28 displays in the display section 9 a list of the measuring administration data recorded in the recording section 31. The list of the measuring administration data includes, for example, the measurer identification and the labels. By this, the controller 28 makes the measuring administration data selectable as an object for the user to instruct analyzing the movement information.

The controller 28 spontaneously instructs the identifying part 29 to analyze the movement information, when conditions 1)-6) below. The conditions are examples, and the user freely set. By this, the result of analyzing the movement information is stored spontaneously in the recording section 31. The controller 28 displays by the display section 9 the result of analyzing the movement information, when the user instructs browsing the result of analyzing the movement information.

1) when the measuring administration data received by the communication section 30 includes an abnormal flag showing abnormality of the glucose concentration;
2) when the measurer identification which is included in the measuring administration data received by the communication section 30 is included none of the plurality of measuring administration data recorded in the recording section 31 (when the user who has the measurer identification measures the glucose concentration);
3) when the number of recording in the recording section 31 the measuring administration data including the measurer identification included in the measuring administration data which is received by the communication section 30 is less than a prescribed number (when experience in measuring the glucose concentration of the user having the measurer identification is few);
4) when a prescribed period of time elapses from previously recording the measuring administration data in the recording section 31 which includes the measurer identification included in the measuring administration data received by the communication section 30 (when the user having the measurer identification measures the glucose concentration after such a long time);
5) when the number of recording in the recording section 31 the measuring administration data including the measurer identification included in the measuring administration data which is received by the communication section 30 is more than a prescribed number (when experience in measuring the glucose concentration of the user having the measurer identification is adequate and the user is experienced); and
6) a prescribed period of time elapses after analyzing the movement information for each of the user having the measurer identification.

The movement determining section 29 reads the measuring administration data which is designated from the recording section 31, when the controller 28 instructs analyzing the movement information. The movement determining section 29 extracts the time of mounting sensor, the time of the sample deposition, the time of starting measuring, the time of ending measuring and the movement information synchronized with those from the measuring administration data which has been read.

Figure 7:
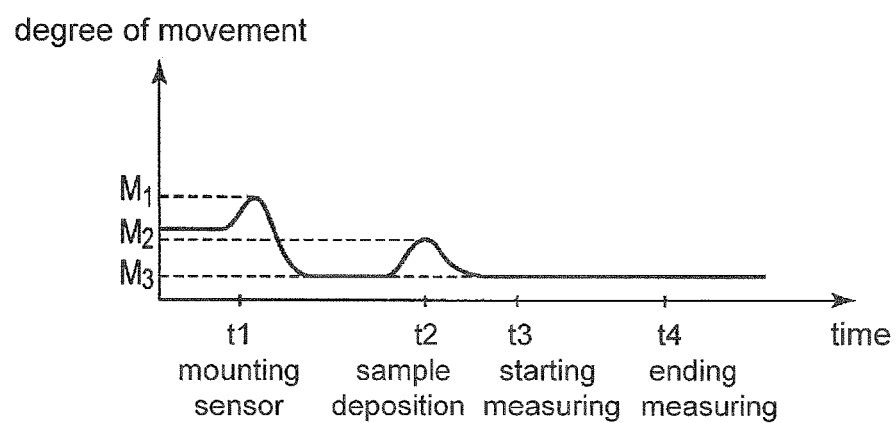
FIG. 7 is a view showing changes a level of movement of the measuring device.

Analyzing the movement information is performed by the movement determining section 29 in a first period (first period, t1-t2), a second period (second period, t2-t3), and a third period (third period, t3-t4), as shown in FIG. 7. The first period is a period from the time of mounting the sensor t1 to the time of the sample deposition t2. The second period is a period from the time of the sample deposition t2 to the time of starting measuring t3. The third period is a period from the time of starting measuring t3 to the time of ending measuring t4. For example, FIG. 7 is an example of the changes in the degree of the movement of the device main body 4 in the X axis 4X which is shown in FIG. 5. The direction of the main body 4 in the X axis 4X is along the direction of mounting the biosensor 7 to the device main body 4. A horizontal axis is for time elapsing, and shows from time before notifying the detection of mounting the biosensor 7 to the time of ending measuring the glucose concentration. A vertical axis shows average values of absolute values of the degree of the changes in the movement transmitted by the movement measuring section 24. Larger the degree of the changes in the movement, larger and more abruptly the device main body 4 is moved. As FIG. 7 shows, a degree of the movement M1 becomes high, as movement is added to the device main body 4 from the biosensor 7 by the handling in mounting the biosensor 7 to the device main body 4. After that, a degree of the movement M2 arises by the movement added to the device main body 4 from a finger of the user via the biosensor 7 by the handling when depositing the blood on the tip of the biosensor 7. After that, a small degree of the movement M3 arises by the handling of the user holding to maintain the posture of the device main body 4. After the time of the sample deposition t2, when the device main body 4 is placed on a table or the like, no degree of the movement arises around a period from the time of starting measuring t3 to the time of ending measuring t4.

Analyzing the movement information in each period is performed by comparing each threshold value with the degree of the changes in the movement in the X axis 4X, the Y axis 4Y, and the Z axis 4Z of the measuring device 1 per unit time. The movement determining section 29 analyzes that the movement of the measuring device 1 is slow within an allowable range, when the degree of the changes in the movement is smaller than the threshold value. The movement determining section 29 analyzes that the movement of the measuring device 1 is fast and over the allowable range, when the amount of changes is more than the threshold value. Whether the movement of the measuring device 1 is slow or fast means whether a momentary acceleration is large or small, and in other words, whether or not an impact to the measuring device 1 is large or small.

The threshold value can be same for all the three axes in each of all the periods. Also, the threshold value can be different in each period corresponding to objectives. The optimum value for the threshold value corresponding to the objective in each period is obtained by experiments and situations with conditions for attaining the objectives An example is described for a threshold value being different in each period. The first period is a period from the time in which the biosensor 7 is mounted to the device main body 4 to the time in which the blood is deposited to the biosensor 7. Therefore, the movement of the measuring device 1 for measuring mainly in the first period is whether or not an impact with a degree being large enough such that the biosensor 7 has the abnormality. The biosensor 7 has a long rectangular shape, as shown in FIG. 2. For this reason, the biosensor 7 easily has a breakage such as a bent, when the impact applies to the measuring device 1 in the longitudinal direction due to the handling while the biosensor 7 is inserted to the measuring device 1. Then, among the thresholds values in the first period, the threshold value particularly in the X axis 4X (forward-and-backward direction of the device main body 4, insertion direction of the biosensor 7) is for detecting the breakage of the biosensor 7. By this, the allowable range is made narrow in order to determine easily the fast movement when the device main body 4 is moved in the forward-and-backward direction, by making the threshold value in the X axis 4X lower.

On the other hand, the handling includes moving the device main body 4 left and right in order for the user to locate the biosensor 7 at a point (location) of the subject person for the deposition. Also, the handling includes putting the device main body 4 on a table or the like after mounting the biosensor 7. These handlings are not easily directly related to the breakage of the biosensor 7. Thus, the threshold value of the Y axis 4Y (right-and-left direction of the device main body 4) and the threshold value of the Z axis 4Z (up-and-down direction of the device main body 4) in the first period are made larger. By this, the allowable range is made wider by making the threshold values in the Y axis 4Y and the Z axis 4Z higher in order not to determine that the movement of the device main body 4 and biosensor 7 in the right-and-left direction and the up-and-down direction of the device main body 4 is the fast movement.

In the second period and the third period, the blood as liquid is deposited on the biosensor 7. In the second period, it is necessary that the blood constantly expands and comes in the sample supply route 15 in the biosensor 7. In the third period, it is necessary that the blood constantly exists on the counter electrode 17 of the biosensor 7, the measurement electrode 18, and the detection electrode 19 after expanding in the sample supply route 15. The second period and the third period have objectives in measuring the glucose concentration with high accuracy. The allowable ranges of the movement in the X axis 4X, the Y axis 4Y, and the Z axis in 4Z in order to satisfy the condition is set and each is made to be the threshold value. Thus, it is preferable to make the allowable range narrower by making the threshold value in the second period and the third period lower than that of the first period.

The movement determining section 29 transmits the result of determining whether or not the movement information in each of the first, second, and the third periods exceeds (becoming an error) the threshold value (allowable range) to the controller 28 after analyzing the movement information. The controller 28 records in the recording section 31 the result of determining with which associating the measuring administration data.

At this time, the controller 28 search the result of determining in the past, when there are cases in which one or a plurality of the result of determining in the first, second, and third periods, which is transmitted from the movement determining section 29, is determined as erroneous. In other words, the controller 28 extracts the measurer identification included in the measuring administration data in which the movement information is completed in analyzing this time from the measuring administration data recorded in the recording section 31. The controller 28 extracts the result of determining in analyzing the movement information being associated with the measuring administration data including the measurer identification that is the same as the measurer identification extracted. The controller 28 obtains the sum of the number of the errors in the result of determining in the past, which is extracted. The controller 28 adds one error this time to the sum of the errors. The controller 28 determines that user's instruction is necessary, when the sum of the number of the errors is over a prescribed number.

The controller 28 can reveal a fact that there are multiple times in measuring with the measuring device 1 moving over the allowable range, by adding the number of the errors, in measuring which the user has performed by now. The allowable range for the degree of the movement is set for measuring the glucose concentration normally, on the above mentioned conditions. Therefore, the fact that the number of the errors becomes over the prescribed number means that there is a problem in the handling of the user in handling the measuring device 1.

Then, the controller 28 implements an instruction program for showing an instruction content which improves the handling of the user. The simplest example is to display a warning on the display section 9 of the administrating device 2. For example, "please do not move abruptly the measuring device after the deposition of the blood" or the like is displayed for the user with the handling recognized as erroneous in the second period. Alternatively, "please instructs not moving the measuring device abruptly after the deposition of the blood" or the like is displayed because the user is an instructor. Further, it is fine to display a video of the movement of measuring in order for the user to learn the handling. It is preferable to emphasize comments for the movement which particularly needs attention in each scene, in displaying the instruction video. Alternatively, not only showing the instruction on the monitor, but it is fine displaying to encourage taking a training of the handling, which is provided by facilities, in order for the user to receive a practical instruction.

Moreover, it is fine that the controller 28 implements a simulation program to replicate the movement of the measuring device 1 on the basis of the movement information. The controller 28 displays on the display section 9 the status of movement and the measuring device 1 as a result of the simulation. At that time, the controller 28 displays warning regarding in which period the movement is problematic on the basis of the result of determining from the movement determining section 29.

These instruction contents to the user are not only displayed on the display section 9 of the administrating device 2, but are fine to be displayed on the display section 5 of the measuring device 1. The controller 28 instructs the communication section 30 to transmit the measurer identification of the user who needs the instruction and the instruction content to the measuring device 1, when the above mentioned instruction is determined to be necessary. The controller 25 of the measuring device 1 records the measurer identification which is received from the administrating device 2 and the instruction content in the recording section 27. The controller 25 displays the instruction content on the display section 5, when the measurer identification read from the input section 6 and the recorded measurer identification match, in other words when the user who needs the instruction is about to measure. By this, the measuring device 1 can instructs the user about the handling when handling the device main body 4.

Figure 8:
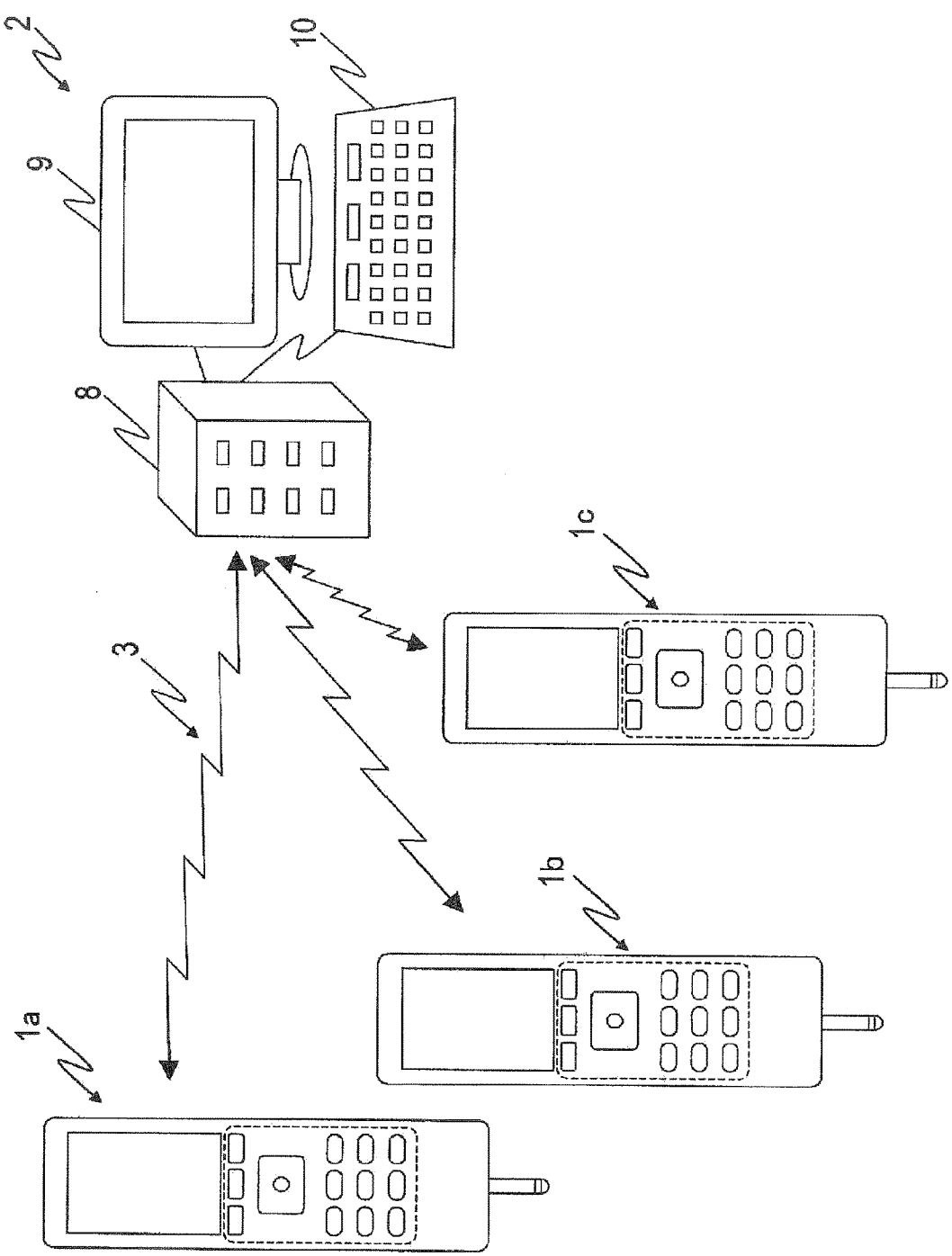
FIG. 8 is view showing an arrangement of a liquid sample measuring system including a plurality of the measuring devices.

As FIG. 8 shows, the administrating device 2 communicates with a plurality of measuring devices 1a-1c, and receives the measuring administration data from each of the plurality of measuring devices 1a-1c. In this case, the controller 28 records the recording section 31 by associating measuring device identification which is a particular number for each of the measuring devices 1a-1c with the measuring administration data. In the above mentioned chain of analyzing the movement information, it is fine to search differently for each of the measurer identification, when searching the measuring administration data for the same measurer identification. This is a search for the result of the particular measuring device by the particular measurer. Alternatively, it is fine to search for measuring administration data against all the measuring administration data recorded in the recording section 31, regardless of the measuring device 1 being a source of obtaining. This is a search for all the results of the particular measurer, while the measuring device is not specified.

Like the latter, the measuring administration data associated with the measurer identification is continuously administered, and is used for analyzing the handling by searching regardless of the measuring device 1 as the source of obtaining. For example, it is effective for measuring the glucose concentration by using randomly the measuring device 1 which is usable for a nurse at a large hospital or the like at that time. Also, it is effective in a case in which the measuring device 1 is replaced for use because of breakage or maintenance.

It is fine to prevent measuring newly until the user confirms the instruction program or the warning displayed, when the controller 28 of the administrating device 2 determines that the particular user needs the instruction. For example, the controller 28 transmits information to all the measuring devices 1 about a ban in measuring which is associated with the measurer identification given to the particular user for instruction. The controller 25 of the measuring device 1 starts monitoring the measurer identification which is input after receiving the information about the ban from the administrating device 2. Then, the controller 25 issues warning when the measurer identification which is banned to be measured and the same measurer identification are read. For example, the controller 25 displays that the measurer identification is banned to be measured, and displays the instruction to confirm the instruction program presented on the administrating device 2 or the measuring device 1 on the display section 5 of the measuring device 1.

The controller 28 can confirm that the user confirms the instruction program by using the input section 10 of itself. In a case in which the controller 28 or the user confirmed the instruction program in one of the measuring devices 1, the controller 28 can recognize by transmitting from the measuring device 1. By this, the controller 28 recognizes the instruction for the handling to the user. After that, the controller 28 of the administrating device 2 transmits information for dismissing the ban for measuring to all the measuring devices 1.

In a case in which the movement information is analyzed as a condition to include the flag for the abnormality in the measuring administration data, the controller 28 confirms whether the abnormality is because of the handling of the user or not, based on the result of determining of the above mentioned movement determining section 29. At this time, the controller 28 confirms the result of determining which is transmitted, after the movement information is analyzed in the movement determining section 29. The controller 28 displays in the display section 9, as if the abnormal value arises for the glucose concentration due to a factor other than the handling of the user when each of the first to third periods is determined as erroneous. The controller 28 transmits the measuring administration data which includes the flag for the abnormal value of the glucose concentration to an information collecting device differently configured from the administrating device 2, in order to analyze the abnormal value precisely.

Figure 9:
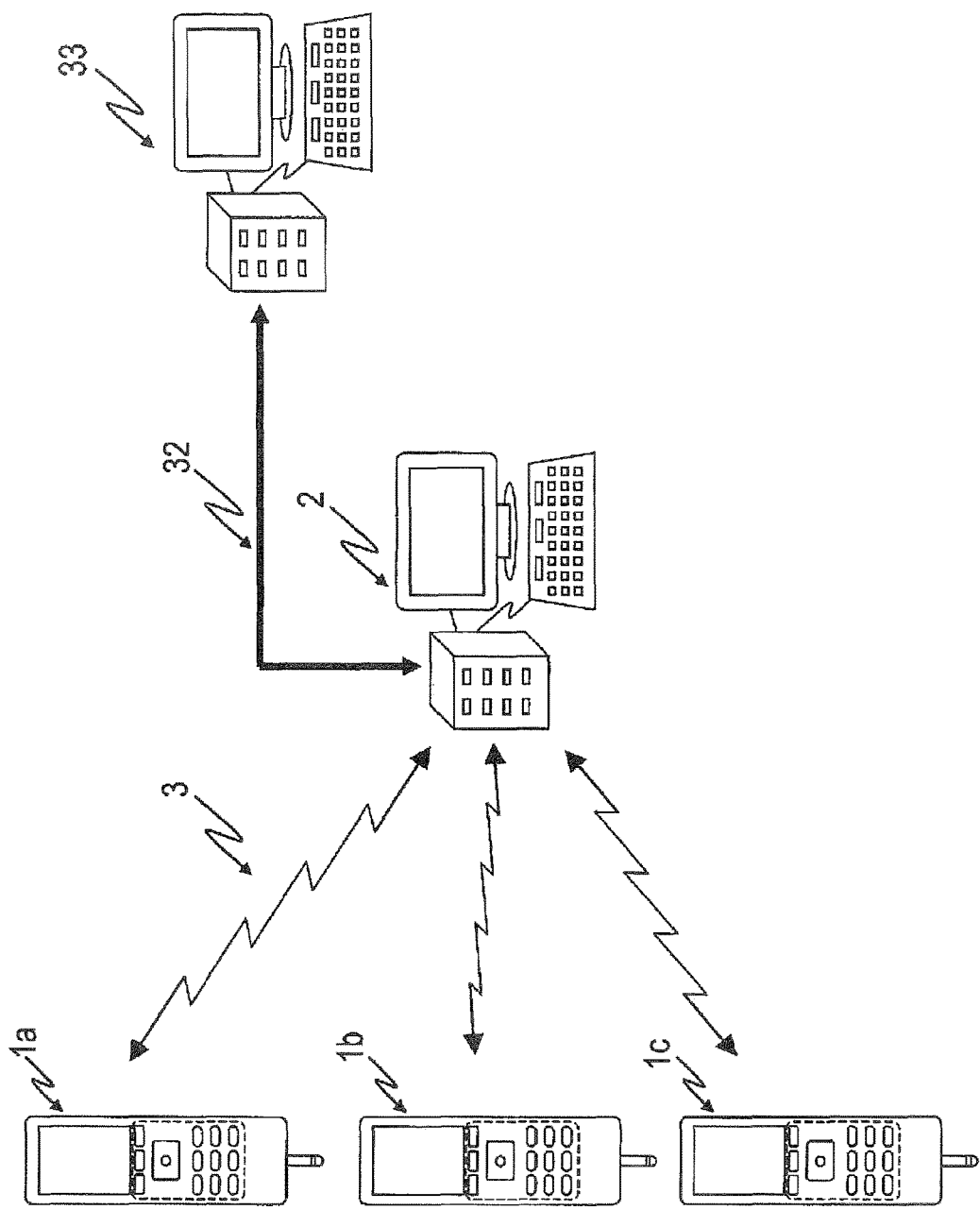
FIG. 9 is a view showing an arrangement of the liquid sample measuring system including an information collection function.

The configuration for it is shown in FIG. 9. FIG. 9 shows an example of the liquid sample measuring system including an information collection function to analyze precisely. In the liquid sample measuring system, the administrating device 2 and the information collecting part 33 are connected by a network 32 using a dedicated line or the internet. The information collecting part 33 is disposed at an administrating department of a sales company or a manufacturer of the measuring device 1, or at an examining department or a monitoring department of a medical institution. The measuring administration data transmitted from the administrating device 2 is consolidated to the information collecting part 33. The consolidated measuring administration data is used for examining for countermeasures or the like by specialist precisely analyzing the factor of the abnormal value.

The information collecting part 33 notifies an involved person of the medical institution immediately when the abnormality is clinical as a result of analyzing the measuring administration data. This notice is performed by transmitting in email or transmitting a signal to boot communication means of a device which the involved person has such as a beeper (beeper). It is fine for the device that the involved person has to include the measuring device 1 other than a mobile device such as a mobile phone.

According to the liquid sample measuring system of the present embodiment, as mentioned above, it is possible to determine whether or not the accuracy of measuring decreases due to the handling of the user, and implement. By this, it is possible to decrease variation of the result of measuring of the measuring device 1.

In the present embodiment, it has discussed about an example in which an acceleration sensor as the movement measuring section is included in the device main body, but it is fine to include two acceleration sensors. It is possible to analyze more accurately the movement information because the movement of the device main body 4 is precisely replicated as long as these multiple acceleration sensors are properly located.

Further, it is preferable to replicate not only the degree of moving but an angle of the device main body 4 by combining a plurality of the acceleration sensors and angle sensors. By this, the posture of the device main body 4 when measuring, from an angle of the device main body 4 can be known. By this, there is an effect on the measuring device 1 which handle the liquid sample to be able to instruct the user by considering moving against the gravity on the liquid.

It is fine that one or a plurality of a two-axes acceleration sensors instead of a three-axes acceleration sensor as the movement measuring section 24.

It is fine that the information collecting part 33 implements and transmits the result to the administrating device 2, instead of the administrating device 2 implementing analyzing the movement information.

Second Embodiment

The above mentioned first embodiment of the liquid sample measuring system is described as an arrangement in which the administrating device 2 analyzes the movement information. In contrast, the liquid sample measuring system of a second embodiment as analyzing the movement information by the measuring device 1 is described.

Figure 10:
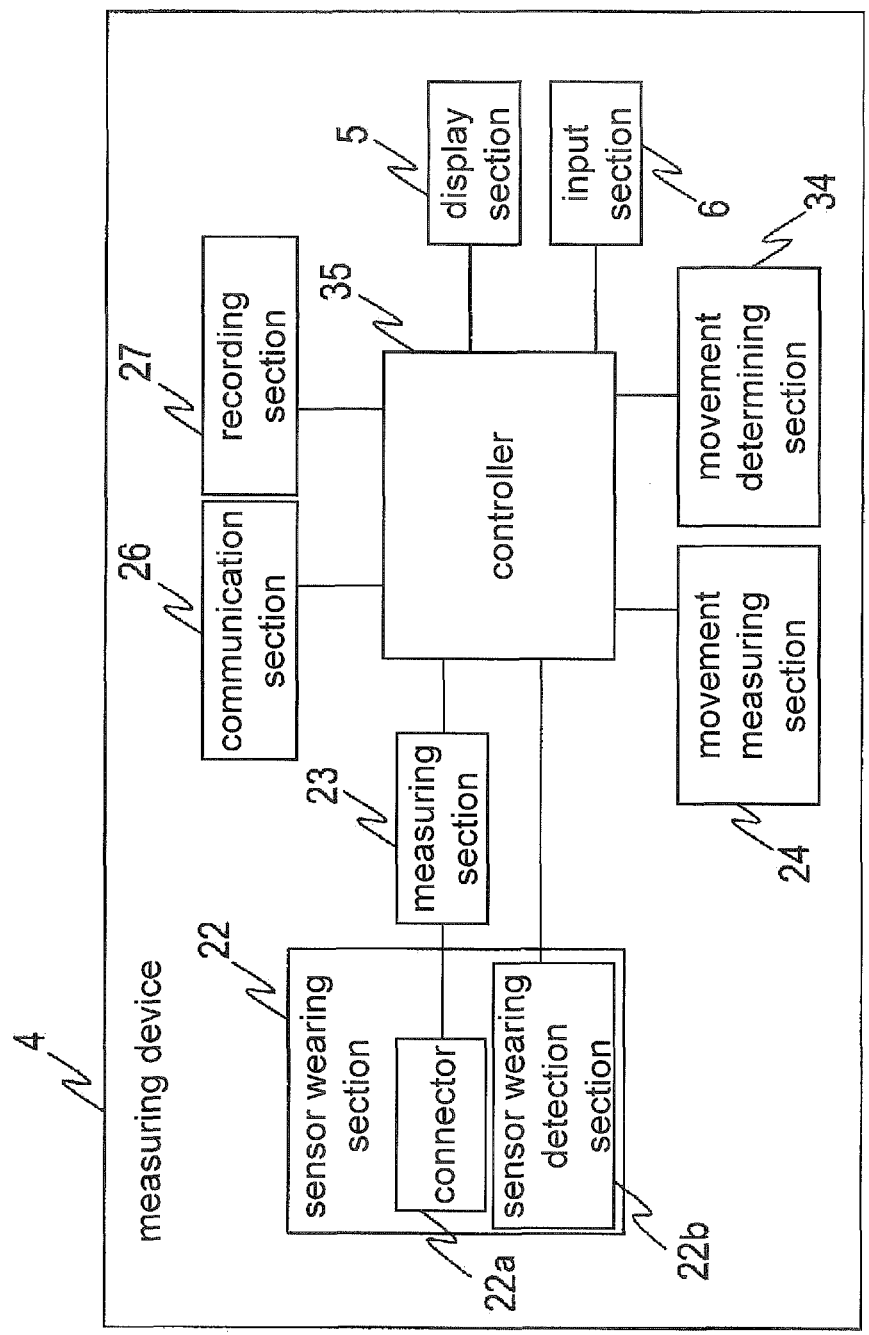
FIG. 10 is a block diagram showing an arrangement of the measuring device of a second embodiment.

FIG. 10 shows a block diagram of the measuring device 1 which can analyze the movement information. Description of the same configuration and movement shown in the block diagram in FIG. 3 are omitted by using the same reference characters. The measuring device 1 is different from the configuration shown in FIG. 3 because including a movement determining section 34 inside the device main body 4. The movement determining section 34 explained in the first embodiment functions same as the movement determining section 29 inside the administrating device 2.

The controller 35 is a thing in which the controller 28 inside functions of the administrating device 2 is added to a controller 25 inside the measuring device 1 described in the first embodiment. In other words, in addition to controlling the measuring device 1, the controller 35 instructs analyzing the movement information to the movement determining section 34, determines whether or not it is necessary to instruct the user on the basis of the result of determining from the movement determining section 34, and controls and presents the instruction program, which are performed by the controller 28 of the administrating device 2.

Figure 11:
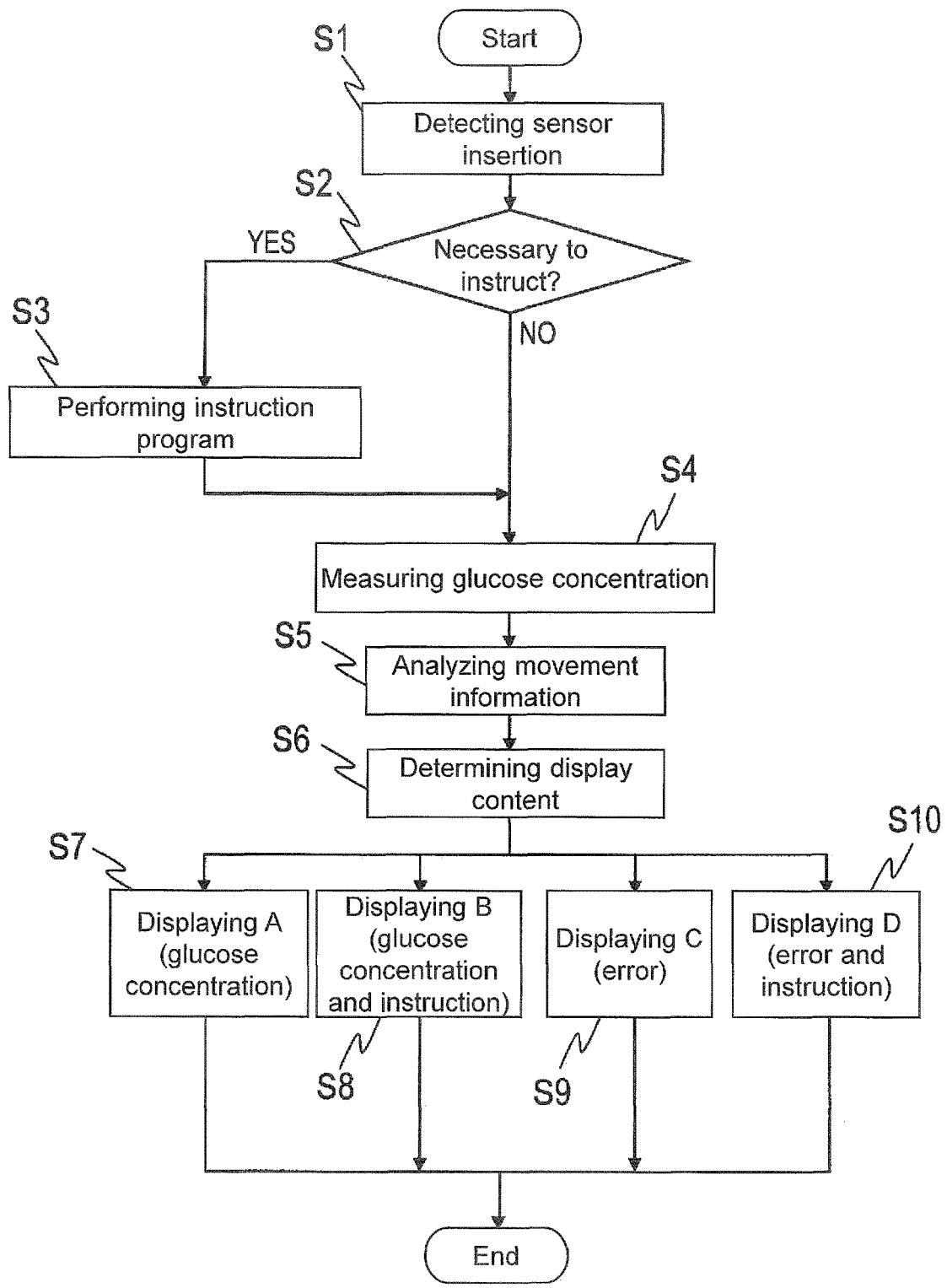
FIG. 11 is a flowchart showing a procedure of the movement of the measuring device including an instruction function to a user.

FIG. 11 is a flowchart showing the movement of the measuring device 1 having the instruction function to the user by the measuring device 1 of the present embodiment.

In step S1, the timing in which the biosensor 7 is mounted to the sensor wearing part 22 by the user is detected by the sensor wearing detection section 22b. The controller 35 recognizes the biosensor 7 being mounted by the notice from the sensor wearing detection section 22b. Before step S1, the preparation of inputting the user identification, the patient identification, and the identification of the biosensor 7 which are necessary for measuring is completed. The controller 35 starts measuring the amount of moving of the device main body 4 by the movement measuring section 24 as well, after mounting the biosensor 7.

In the present embodiment, it is fine that the measuring device 1 is the measuring device 1 for a person who is the user as the measurer and the patient as the subject person at the same time. In this case, inputting the user identification (measurer identification) and the patient identification (subject person identification) which is implemented each time when the measurer and the subject person is not same is omitted. Therefore, when the measuring device 1 is for personal use, and when the biosensor 7 is detected in step S1 to be mounted to the sensor wearing part 22, it is fine that the controller 25 controls the display section 5 and the input section 6 to make the user input the identification of the biosensor 7.

In step S2, the controller 35 confirms whether or not there is the measuring administration data, which is the result of measuring in the past, in the recording section 27 more than a prescribed times (for example 3 times). When the measuring administration data exists more than the prescribed times, the controller 35 extracts the prescribed number of the result of analyzing the movement information by chronologically going back from the measuring administration data which is closest to the present time. The controller 35 determines that the instruction is necessary for the handling, when the result of analyzing of the extracted movement information is all erroneous. On the other hand, partially or entirely the result of analyzing of the movement information is not erroneous, the controller 35 determines that the instruction for the handling is not necessary.

When the instruction for the handling is determined to be necessary in step S2, the controller 35 proceeds to step S3. In step S3, the controller 35 displays "confirmation of precaution is necessary" in the display section 5. By this, the controller 35 presents encouragement to the user of confirming the instruction program. After that, when the user requests confirming the instruction program by using the input section 6, the controller 35 displays the instruction program which is stored in the recording section 27 on the display section 5. On the other hand, when the instruction for the handling is not necessary in step S2, the controller 35 waits for the blood being deposited, and proceeds to step S4.

In step S4, the blood is deposited on the biosensor 7, and the glucose concentration is measured by the measuring section 23, as discussed in the first embodiment. At this time, the controller 35 detects the blood being deposited on the biosensor 7, the movement information from the time when the sensor is mounted to the time of the sample deposition (first period) is recorded in the recording section 27. Also, when the blood is lead inside the biosensor 7 and measuring the glucose concentration is started, the controller 35 records in the recording section 27 the movement information from the time of sample deposition to the time of starting measuring (second period). Further, when measuring the glucose concentration is ended, the controller 35 records in the recording section 27 the movement information from the time of starting measuring to the time of ending measuring (third period). The result of measuring the glucose concentration and the movement information are clumped together and recorded in the recording section 27 as the measuring administration data.

The blood deposition is detected on the biosensor 7 during step S3, it is forced to finish step S3 and proceed to step S4. For example, even in a stated in which displaying the instruction program is performed or in which the request for displaying the instruction program from the user is waited, it proceed to step S4. In a case in which the blood is prepared in an emergency situation and the user performs puncturing the patient beforehand, this prevents the prepared blood from being dry and being wasted while waiting the instruction program for ending. The controller 35 records whether the instruction program of step S3 is completed or interrupted as a history in the recording section 27, when proceeding to step S4.

The controller 35 proceeds to step S5 and instructs the movement determining section 34 to analyze the movement information, when measuring the glucose concentration ends, and the measuring administration data is recorded in the recording section 27. At this time, the movement determining section 34 reads the movement information recorded in step S4 from the time when the sensor is mounted to the time of ending measuring. Then, the movement determining section 34 analyzes the movement information in each of the first, second, and third periods for the read movement information, just as the movement determining section 29 described in the first embodiment.

Next, the controller 35 proceeds to step S6 and determines the display contents on the display section 5. When measuring the glucose concentration in step S4 ends, the controller 35 reads the measuring administration data recorded on the recording section 27 from the recording section 27, and the result of measuring the glucose concentration and the result of analyzing the movement information are confirmed.

First, the controller 35 confirms whether or not the result of measuring the glucose concentration is a measuring value within the range. Next, the controller 35 confirms whether or not there is a period in which the result of analyzing the movement information is erroneous. The controller 35 chooses the display content on the display section 5 among a plurality of display contents which are prepared beforehand, on the basis of the result of determining the glucose concentration and the result of analyzing the movement information. Here, the range of the measuring value for determining the result of measuring the glucose concentration is further wider than the range necessary for warning the user for normal low glucose concentration and normal high glucose concentration. For this reason, a threshold value to determine the high glucose concentration and a threshold value to determine the low glucose concentration are set for the glucose concentration. Further, a range with a threshold value larger than the threshold value for the high glucose concentration and a threshold value lower than the low threshold value for the low glucose concentration in order to determine an abnormal measuring range is set. The range set between the two threshold values in order to determine the abnormal measuring range is a range for not determining the abnormal range and the "prescribed range" which will be described hereinafter.

In a case in which the result of measuring the glucose concentration is within the prescribed measuring range and there is no period in which the result of analyzing the movement information is erroneous, processing advances in step S7. The controller 35 displays at least the result of measuring (display A) the glucose concentration which has been measured on the display section 5. At this time, when the result of measuring the glucose concentration is within the prescribed range but determined as the high glucose concentration or the low glucose concentration, the controller 35 makes the display section 5 display also warning for the low glucose concentration or the high glucose concentration.

In a case in which the result of measuring the glucose concentration is within the prescribed measuring range and there is a period in which the result of analyzing the movement information is erroneous, processing advances in step S8. The controller 35 makes the display section 5 display (display B) at least the result of measuring the glucose concentration which has been measured, and the instruction program to the user. For example, in a case in which the degree of the movement in the second period is determined to be erroneous, "please do not move abruptly after the blood deposition" as the instruction program is displayed. At this time, when the result of measuring the glucose concentration is within the prescribed range but determined as the low glucose concentration or the high glucose concentration, displaying the warnings of the low glucose concentration or the high glucose concentration is also performed.

In a case in which the result of measuring the glucose concentration is outside the prescribed measuring range and there is no period in which the result of analyzing the movement information is erroneous, processing advances in step S9. The controller 35 makes the display section 5 not display (display C) the result of measuring the glucose concentration but display the warning of the measuring error. At this time, it is fine that the controller 35 displays the instruction of measuring again.

In a case in which the result of measuring the glucose concentration is outside the prescribed measuring range and there is a period in which the result of analyzing the movement information is erroneous, processing advances in step S10. The controller 35 makes the display section 5 not display the result of measuring the glucose concentration but display the warning of the measuring error and the instruction program to the user. For example, in a case in which the degree of the movement in the second period is determined to be erroneous, "please do not move the measuring device abruptly after the blood deposition" as the instruction program is displayed. Further, the controller 35 makes the display section 5 display the instruction to measure again.

Like this, in the present embodiment, a timing in which the movement information is analyzed is right after the glucose concentration is measured by the measuring section 23. With regards to the timing, the measuring device 1 instructs the user in the handling as needed before measuring the glucose concentration, or right after measuring the glucose concentration, or the both.

Instructing the user in the handling before measuring the glucose concentration has an effect of encouraging doing the handling for measuring with strong notion because the user has a fresh memory of the contents of the instruction. For this, it is effective as a countermeasure against the decrease of the measuring accuracy due to user's handling, when measuring the glucose concentration is about to start.

Also, instructing the user right after measuring the glucose concentration has an effect of pointing out things which have to be improved, while the user has the fresh memory of his/her handling right after measuring. For this, it is effective as a countermeasure against the decrease of the measuring accuracy due to user's handling, when the user measures the glucose concentration from the next time.

Like this, the display section 5 can display the instruction program before measuring the glucose concentration on the basis of the result of determining of the movement recorded in the recording section 27. Also, the display section 5 can displays the instruction program right after measuring the glucose concentration on the basis of the result of determining the movement in the periods including the one in which measuring is being performed after measuring the glucose concentration.

Further, the present embodiment discloses a second timing to analyze the movement information. The second timing is when the user, or a pursuer of the medical institution such as a doctor or a medical coordinator of a medical institution instructs the controller 35 to analyze the movement information by using the input section 6.

Time in which the pursuer of the medical institution instructs analyzing the movement information is when, for example, an individual patient comes to a hospital with the measuring device 1 which is used at home, and takes a medical examination by a doctor. The doctor confirms the measured value of the glucose concentration in a daily life of the patient recorded in the recording section 27 of the measuring device 1, and can instruct the patient in dispensing and consult daily the daily life. On this occasion, confirming whether or not the daily handling, when the patient measures, is properly performed by analyzing the movement information.

The controller 35 makes the display section 5 display a menu and receives the instruction from the user, as a movement other than when measuring the glucose concentration. The menu which the display section 5 displays includes an item to display the measured values of the glucose concentration measured in the past and recorded in the recording section 27, for example. Other items include maintenance of the measuring device 1 and the like. In the item of the maintenance, there is an item for instructing analyzing the movement information.

When instructed from the user to analyze the movement information via the input section 6, the controller 35 instructs the movement determining section 34 to analyze the movement information. When the user selects the items for analyzing the movement information from the menu displayed on the display section 5 by using the input section 6, the controller 35 makes the display section 5 display the result of measuring the glucose concentration and the date and the time on which the result of measuring is obtained, namely the date and the time on which measuring the glucose concentration is performed from the recording section 27. When there are the results of measuring for more than multiple time of measuring in the recording section 27, it is displayed in the list.

Then, the controller 35 makes the user select, in analyzing the movement information, in which date and time in which the glucose concentration is measured, in an interactive way by using the display section 5 and the input section 6. The controller 35 instructs the movement determining section 34 which date and time the movement information is analyzed by following the input from the input section 6. The movement determining section 34 reads, from the recording section 27, the movement information for the date and the time instructed by the controller 35, analyzes the movement information, and transmits the result of analyzing to the controller 35. The controller 35 makes the display section 5 display the result of measuring the glucose concentration as mentioned above and the date and time in which the result of measuring is obtained, as well as the result of analyzing the movement information which is transmitted by the movement determining section 34. It is fine that the user instructs analyzing, at one time, the movement information obtained from a plurality of times of measuring.

By this, for example, when the abnormal value is recorded in the measured value of the glucose concentration, a doctor confirms whether or not it is due to the handling of the patient, and determines how to respond to the patient. Also, when the abnormal value is not recorded in the measured value of the glucose concentration, whether or not there is a problematic movement in the handling is confirmed. By this, it is possible for the doctor to instruct the patient for the handling in order to suppress the decrease in the accuracy in measuring due to patient's handling being inappropriate which will happen in the future.

According to the measuring device of the present embodiment, it is possible that the measuring device 1 alone determines whether or not the accuracy of measuring decreases due to the handling of the user, and takes an appropriate countermeasure. By this, the variation of the result of measuring by the measuring device 1 can be decreased.

Third Embodiment

Figure 12:
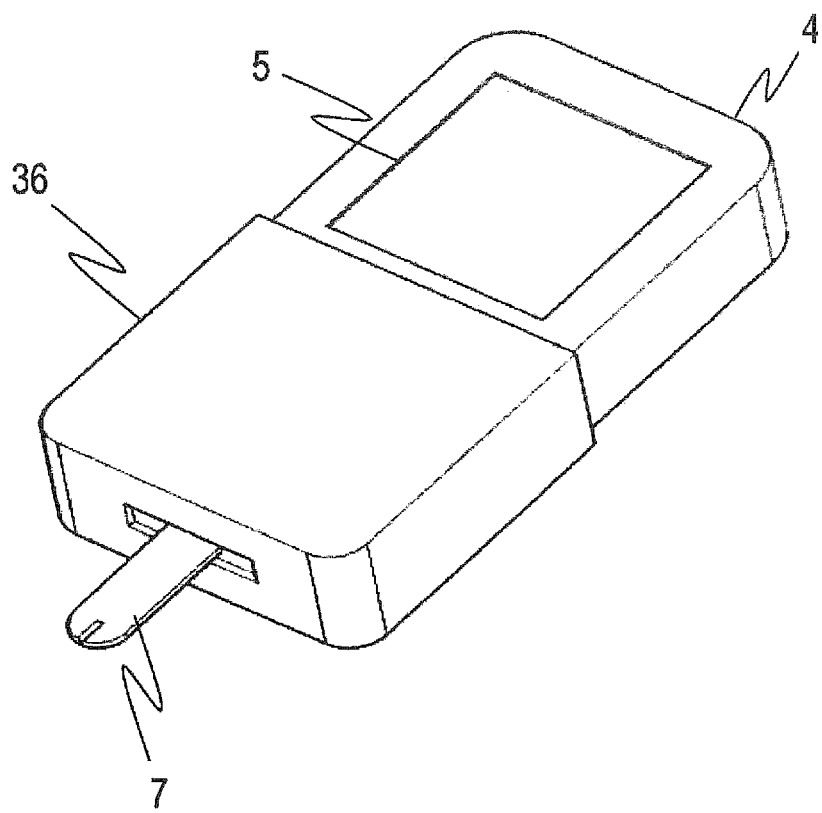
FIG. 12 is a diagonal perspective view of an appearance of the measuring device of a third embodiment.
Figure 13:
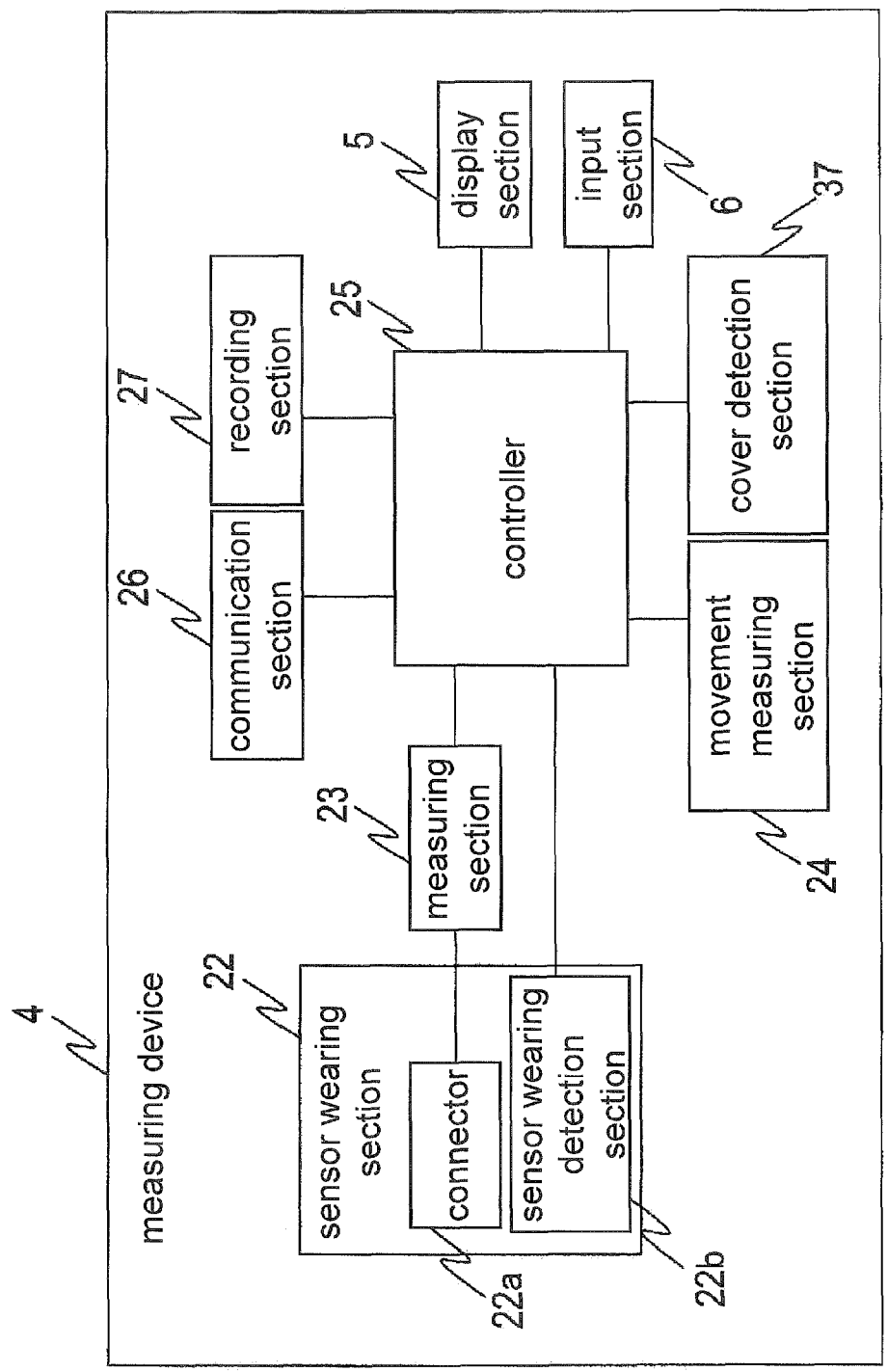
FIG. 13 is a block diagram showing the measuring device of the third embodiment.

The measuring device 1 of the present embodiment is, in addition to the above mentioned embodiments, an arrangement in which it is possible to equip the cover 36 on the device main body 4. FIG. 12 is a view of an appearance of the measuring device which mounts the cover 36 on the device main body 4. FIG. 13 is a block diagram of the measuring device on which the cover is possible to be mounted.

As FIG. 12 shows, the measuring device 1 of the present embodiment is a thing in which the cover is mounted on the device main body 4 which measures the movement information as mentioned above. The cover 36, as shown in the figures, is detachably mounted on the device main body 4 so as to cover from a side surface on which the biosensor 7 is mounted to the outside of the device main body 4. In FIG. 12, the cover 36 is shaped in a way to cover an upper part of the input section 6, but it is fine to cover the upper part of the display section 5. In contrast, it is also fine that the cover 36 does not cover the display section 5 and the input section 6, but is shaped in the way to cover the side surface on which the biosensor 7 is mounted. Alternatively, it is also fine that the cover is formed so as to cover entirely the device main body 4.

The purpose of the cover 36 being mounted on the device main body 4 is to prevent the blood to be erroneously deposited on the device main body 4 when the blood of the subject person is to be deposited to the biosensor 7. Therefore, the cover 36 is replaced each time when the glucose concentration is measured, or when the blood is deposited. By this, it is possible to prevent that infection happens to a third person other than the subject person by adhering the blood on the device main body 4.

For this reason, the measurer (user) must keep the cover 36 mounted on the device main body 4 as doing (handling) in measuring, and if cannot, the instruction to the user is necessary.

Then, as FIG. 13 shows, a cover detection section 37 is added to the device main body 4 of the measuring device 1. The cover detection section 37 detects whether or not the cover 36 is mounted on the device main body 4 and transmits to the controller 25. An ordinary sensor is fine for the arrangement to detect the cover 36 being mounted on the device main body 4. For example, the cover detection section 37 is constituted by a mechanical contact-type switch which switches on and off by physical contacts when the cover 36 is mounted on the device main body 4. Alternatively, it is fine that the cover detection section 37 is arranged to have an optical sensor which detects the cover 36 being mounted depending on changes of an amount of received light due to the cover 36 covering the device main body 4. Other than that, a thing that detects by using electrical or magnetic characteristic is fine. When the cover detection section 37 detects the cover 36 being mounted by the optical sensor, it is fine to adjust contrast and light intensity of the display section 5 depending on the received amount of light by the cover detection section 37. For example, in a case in which the cover 36 covers the display section 5, when the cover 36 is mounted, brightness and lightness of the display section 5 is increased in order to prevent that the display section 5 is difficult to see by the existence of the cover 36.

The controller 35 records in the recording section 27 by adding in the measuring administrating data the result of detecting, which the cover detection section 37 transmits, whether or not the cover 36 is mounted to the device main body 4 from the time of mounting the sensor to the time of ending measuring.

The controller 28 of the administrating device 2 detects whether or not the cover 36 is mounted when the movement information is analyzed as described in the above mentioned embodiment. The controller 28 displays the warning or the instruction program to the user when the cover 36 is not mounted while measuring the glucose concentration. For example, "it is necessary to mount the cover while measuring the glucose concentration" or the like is displayed.

Like this, according to the liquid sample measuring system of the present embodiment, the user, in addition to determining the influence of the decrease in the measuring accuracy by user's handling, it can be observed whether the user measures in a right procedure and the correction can be performed if wrong.

In the beginning, the cover 36 is fine to have no opening on the side surface on which the biosensor 7 is mounted and the cover 36 is fine to cut by an end of the biosensor 7 which is held by the device main body 4 when the biosensor 7 is mounted to the device main body 4.

The sensor wearing part 22 is configured in a middle part of the side surface of the device main body 4, and it is fine that the cover 36 can be mounted regardless of which direction an upper surface and a lower surface face. Alternatively, in a case in which the sensor wearing part 22 is configured at a place off from the middle part, it is fine to display on the cover 36 in order to recognize the direction for mounting to the device main body 4. Further, depending on forming, it is fine that the user recognizes the direction of mounting. For example, when a translucent material is used for the cover 36, a degree of transparency of a surface corresponding to the display section 5 is high, and a degree of transparency of an opposite side surface is low.

The example of measuring the glucose concentration in the blood in which the electrochemical biosensor 7 is mounted to the measuring device 1 and the blood of the living subject as the sample liquid is deposited, but it is not limited in the all the embodiments.

Blood, urine, interstitial fluid, or the like which is practically a sample, in a form of liquid concentrate or liquid solution, from a living subject is applied as the sample liquid. Alternatively, it is fine to be products of experiment or products of pseudo of those samples. Further, a process solution after preprocess of degeneration and a chemical change be used. Alternatively, in a case in which a control liquid for correcting the measuring device 1 is used, the present invention is applicable.

For the measuring object such as sugar group, lactic acid, various cholesterols, nucleic acid, DNA, immune body, antigen, protein, hormone, bacteria, enzyme, drug, antibiotic, medical composition, marker, chemical substance, the present invention is applicable for all that develop and determine quantity in the sample.

The biosensor 7 having a structure such as a chamber storing the sample which has been deposited and expanding by a function of membrane or flow passage after the blood is deposited is used. Alternatively, instead of the biosensor 7, a biochip or DNA chip which is used in the preprocessing such as hybridization, blood cell contraction, or blood cell breakage, can be used. In other words, the present invention is applied to all configurations in which there is a chance that the result of measuring is affected by the movement or the posture of the sensor or the chip from supplying the sample liquid to the sensor or the chip to the end of measuring.

Further, a supply method for supplying the sample liquid to the biosensor 7 is fine by supplying not only directly from the living subject for the deposition but also from a syringe, a cartridge, or a preprocessing reservoir. It is fine to measure the object in a state in which the cartridge or the preprocessing reservoir for supplying the sample liquid is mounted to the biosensor 7.

Further, measuring by the measuring device 1 includes all measuring method which can perform by the hand-held type measuring device such as an optical type or a magnetic type.

The entire contents of Japanese Patent Application No. 2011-283197 (filing date: Dec. 26, 2011) is herein incorporated.

The above mentioned embodiment is an example of the present invention. For this reason, needless to say, the present invention is not limited to the above mentioned embodiments, and various modifications, although for a different embodiment, can be made depending on designs, as long as the modifications do not deviate from technical ideas of the present invention.

INDUSTRIAL APPLICABILITY

According to the above mentioned liquid sample measuring system and the measuring device, when measuring the biological information from the liquid sample of the living subject, it is possible to confirm whether or not the handling of the user is outside the allowable range, and to display the appropriate countermeasure. The above mentioned liquid sample measuring system is useful as a measuring administration incorporation system, or the like, which includes a measuring device and a computer with an administration program thereon.

What is claimed is:

1. A liquid sample measuring system, comprising:
   a measuring device including a housing, a measuring section, and a movement measuring section,
   the measuring section measuring biological information from a liquid sample of a living subject, and disposed inside of the housing, and
   the movement measuring section measuring movement information of the housing, and disposed inside the housing; and
   an administrating device including a movement determining section,
   the movement determining section comprising a processor programmed to analyze the movement information and determine whether or not an acceleration of the housing is larger than a threshold value indicating that a movement of the housing is over an allowable range, and wherein:
   a display section is provided in the measurement section or the administrating device;

a biosensor is detachably mounted to the housing and the biosensor accepts a sample deposition of the liquid sample of the living subject;

the processor is further programmed to determine the acceleration of the housing during a time from when the biosensor is mounted to the housing to when measuring the biological information by the measuring section ends;

the processor is further programmed to determine whether the acceleration of the housing is within the allowable range in each of a first period, a second period, and a third period;

the first period being a first time period from a mounting of the biosensor to the sample deposition;

the second period being a second time period from the sample deposition to a start of measurement of the biological information; and the third period being a third time period from the start of measurement to an ending of measurement of the biological information; and the processor further programmed to display a period in which the acceleration of the housing is outside the allowable range on the display section.

2. The liquid sample measuring system according to claim 1, wherein:

the processor is further programmed to set a different allowable range for each of the first, the second, and the third periods, and determines whether the degree of the change in the movement in each of the first, the second, and the third periods is within each respective allowable range for the first, the second, and the third periods.

3. The liquid sample measuring system according to claim 2, wherein:

the processor is further programmed to determine whether or not an allowable range of movement in a direction in which the biosensor is inserted to the housing is narrower than an allowable range of the degree of the change in the movement in other directions.

4. The liquid sample measuring system according to claim 2, wherein:

the processor is further programmed to determine whether or not an allowable range of the acceleration of the housing in a right direction and a left direction is wider than an allowable range in other directions.

5. The liquid sample measuring system according to claim 2, wherein:

the processor is further programmed to detect, in the second period, a state in which the liquid sample is not stably let to the biosensor based on the allowable range of the acceleration of the housing.

6. The liquid sample measuring system according to claim 2, wherein:

the processor is further programmed to detect, in the third period, a state in which the liquid sample does not stably exist on an electrode of the biosensor based on the allowable range of the degree of the change in the movement.

7. The liquid sample measuring system according to claim 1, further comprising:

a display section indicates that the acceleration of the housing is outside the allowable range when the processor determines that the acceleration of the housing is outside the allowable range.

8. The liquid sample measuring system according to claim 7, wherein:

the processor is further programmed to have the display further instruct a user how to handle the measuring device according to an instruction program.

9. The liquid sample measuring system according to claim 8, wherein:

the processor is further programmed to record a measurer identification;

the administrating device transmits measurer identification information to a plurality of measuring devices, and transmits the instruction program with the measurer identification information;

the measurer identification information identifying a measurer needing instruction handling the device via the instruction program; and when the measurer identification input in a measurement by the measuring section matches a measurer identification transmitted from the administrating device, the display section displays the instruction program.

10. The liquid sample measuring system according to claim 1, wherein:

the processor is further programmed to determine whether biological information measured by the measuring section is an abnormal value;

the administrating device further transmits the biological information to an information collecting device; and when the acceleration of the housing is within the allowable range and the biological information is an abnormal value, the administrating device transmits the biological information to the information collecting device.

11. The liquid sample measuring system according to claim 1, further comprising:

a cover detachably mounted to the housing, and covers at least a portion of the housing;

a cover detection section detects whether the cover is mounted when measuring the biological information is performed by the measuring section; and a display section instructs a user how to handle the measuring device according to an instruction program when measuring is performed by the measuring section in a state in which the cover is not mounted.

12. The liquid sample measuring system according to claim 1, wherein:

the housing further includes a width-direction center line and a longitudinal-direction center line; and the movement measuring section is disposed off of both the width-direction center line and the longitudinal-direction center line.

13. A measuring device, comprising:

a housing;

a display section;

a measuring section measuring biological information from a liquid sample disposed in the housing;

a movement measuring section measuring movement information of the housing, the movement measuring section disposed in the housing; and a movement determining section comprising a processor programmed to analyze the movement information, and to determine whether or not an acceleration of the housing is larger than a threshold value indicating that a movement of the housing is over an allowable range wherein:

a biosensor is detachably mounted to the housing and the biosensor accepts a sample deposition of the liquid sample of the living subject;

the processor is further programmed to determine the acceleration of the housing during a time from when the biosensor is mounted to the housing to when measuring the biological information by the measuring section ends;

the processor is further programmed to determine whether the acceleration of the housing is within the allowable range in each of a first period, a second period, and a third period;

the first period being a first time period from a mounting of the biosensor to the sample deposition, the second period being a second time period from the sample deposition to a start of measurement of the biological information; and the third period being a third time period from the start of measurement to an ending of measurement of the biological information; and the processor is further programmed to display a period in which the acceleration of the housing is outside the allowable range on the display section.

14. The measuring device according to claim 13, further comprising:

a recording section including a result;

a display section displays an instruction program that instructs a user how to handle the housing;

the processor is further programmed to determine whether the instruction program should be displayed based on the result, and programmed to determine whether the instruction program should be displayed while performing measurement; and the display section further displays the instruction program before the measuring section measures the biological information when the processor determines that the instruction program should be displayed, and to display the instruction program right after the measuring section measures the biological information when the processor determines that the instruction program should be displayed while performing measurement.

15. The measuring device according to claim 13, further comprising:

a biosensor accepts the liquid sample, and which is detachably mounted to the housing.

16. The liquid sample measuring system according to claim 1, wherein: the threshold value indicates that a movement of the housing per unit time is over an allowable range.

17. The liquid sample measuring system according to claim 13, wherein: the threshold value indicates that a movement of the housing per unit time is over an allowable range.

* * * * *